(12) United States Patent
Florio et al.

US009745554B2

(10) Patent No.: US 9,745,554 B2
(45) Date of Patent: Aug. 29, 2017

(54) METHOD OF IMPROVING CELL PROLIFERATION OF PANCREATIC PROGENITOR CELLS IN A PANCREATIC CELL CULTURE

(75) Inventors: Monica Florio, Woodland Hills, CA (US); Aleksandar Francki, Santa Monica, CA (US); Wen-Ghih Tsang, Sherman Oaks, CA (US)

(73) Assignee: ReNeuron, Inc., Guildford (GB)

( * ) Notice: Subject to any disclaimer, the term of this patent is extended or adjusted under 35 U.S.C. 154(b) by 1404 days.

(21) Appl. No.: 12/161,677

(22) PCT Filed: Jan. 18, 2007

(86) PCT No.: PCT/US2007/001555
§ 371 (c)(1),
(2), (4) Date: Jul. 21, 2008

(87) PCT Pub. No.: WO2007/084730
PCT Pub. Date: Jul. 26, 2007

(65) Prior Publication Data
US 2010/0311166 A1    Dec. 9, 2010

Related U.S. Application Data

(60) Provisional application No. 60/760,445, filed on Jan. 20, 2006.

(51) Int. Cl.
*C12P 21/00*    (2006.01)
*C12N 5/071*    (2010.01)
*A61K 35/12*    (2015.01)

(52) U.S. Cl.
CPC ......... *C12N 5/0676* (2013.01); *C12N 5/0677* (2013.01); *A61K 2035/126* (2013.01); *C12N 2501/105* (2013.01); *C12N 2501/135* (2013.01); *C12N 2501/48* (2013.01); *C12N 2501/70* (2013.01); *C12N 2509/00* (2013.01); *C12N 2533/32* (2013.01); *C12N 2533/74* (2013.01)

(58) Field of Classification Search
None
See application file for complete search history.

(56) References Cited

U.S. PATENT DOCUMENTS

| | | | |
|---|---|---|---|
| 6,562,620 B2 | 5/2003 | Rosenberg et al. | |
| 2002/0172665 A1 | 11/2002 | Rosenberg et al. | |
| 2006/0281174 A1* | 12/2006 | Xu et al. | 435/325 |
| 2007/0072292 A1 | 3/2007 | Tsang et al. | |
| 2007/0166288 A1 | 7/2007 | Murry et al. | |

OTHER PUBLICATIONS

Movassat et al (Diabetologia, 2003. vol. 46: pp. 822-829).*
Dickson, L. M. et al. (Aug. 2004). "Pancreatic Beta-Cell Growth and Survival in the Onset of Type 2 Diabetes: A Role for Protein Kinase B in the Akt?," *American Journal of Physiology—Endocrinology and Metabolism* 287:E192-E198.
Florio, M. et al. (2006). "Activation of Akt1 in Primary Human Pancreatic Cells Improves Survival and Proliferation of Endocrine Lineage Cells," Abstract 1525-P, *Diabetes* 55(Suppl. 1):A354.
Garcia-Ocana, A. et al. (2001). "Using Beta-Cell Growth Factors to Enhance Human Pancreatic Islet Transplantation," *The Journal of Clinical Endocrinology and Metabolism* 86(3):984-988.
Lingohr, M. K. et al. (Aug. 2002). "Pancreatic Beta-Cell Growth and Survival—A Role in Obesity-Linked Type 2 Diabetes?," *Trends in Molecular Medicine* 8(8):375-384.
Nakano, M. et al. (Aug. 2004). "Caspase-3 Inhibitor Prevents Apoptosis of Human Islets Immediately After Isolation and Improves Islet Graft Function," *Pancreas* 29(2):104-109.
Supplementary European Search Report mailed Mar. 9, 2009, for EP Application No. 07718278.0 filed Jan. 18, 2007, 6 pages.
International Search Report and Written Opinion mailed Sep. 27, 2007, for PCT Application No. PCT/US07/01555 filed Jan. 18, 2007, 10 pages.
Montolio, M. et al. (2005). "Short-Term Culture with the Caspase Inhibitor z-VAD.fmk Reduces Beta Cell Apoptosis in Transplanted Islets and Improves the Metabolic Outcome of the Graft," *Cell Transplantation* 14:59-65.
Office Action received for Australian Patent Application No. 2007207434, mailed on Jan. 24, 2012, 2 pages.
Office Action received for Canadian Patent Application No. 2,637,843, mailed on May 23, 2013, 3 pages.
Decision to Grant received for Japanese Patent Application No. 2008-551438, mailed on Dec. 17, 2013, 3 pages (Official copy only). (See Communication under 37 CFR § 1.98(a) (3)).
Office Action received for Japanese Patent Application No. 2008-551438, mailed on Aug. 20, 2013, 4 pages (2 pages of English Translation and 2 pages of Office Action).
Office Action received for Japanese Patent Application No. 2008-551438, mailed on Jun. 5, 2012, 6 pages. (3 pages of English translation and 3 pages of Office Action).
International Preliminary Report on Patentability received for PCT Patent Application No. PCT/US2007/001555, issued on Jul. 22, 2008, 7 pages.
Aikin et al., "Cross-Talk between Phosphatidylinositol 3-Kinase/AKT and c-Jun NH2-Terminal Kinase Mediates Survival of Isolated Human Islets", Endocrinology, vol. 145, No. 10, Oct. 2004, pp. 4522-4531.

* cited by examiner

*Primary Examiner* — Celine Qian
(74) *Attorney, Agent, or Firm* — Morrison & Foerster LLP

(57) ABSTRACT

The invention relates to the discovery that the proliferation and survival of pancreatic progenitor cells can be enhanced by contacting the cells with, (1) a caspase inhibitor sufficient to reduce apoptosis in the pancreatic endocrine cells; and, (2) a growth factor in an amount sufficient to increase the level of activated Akt in the pancreatic endocrine cells.

10 Claims, 8 Drawing Sheets

Figure 1. Caspases are Active in the Adherent Fraction of Cultured Human Pancreatic Cells Figure 2. Survival Medium Rescues Human Pancreatic Cells from Apoptosis Figure 3. Cells Grown in Survival Medium Show Increased Proliferation Figure 5. Increase in the Number of Cells expressing C-peptide and PDX-1 following treatment of Pancreatic Cultures with Survival Medium Figure 8. Static Glucose Expression and Gene Expression of Pancreatic Cells Grown in Control Medium or Survival Medium and then Treated with Differentiation Factors
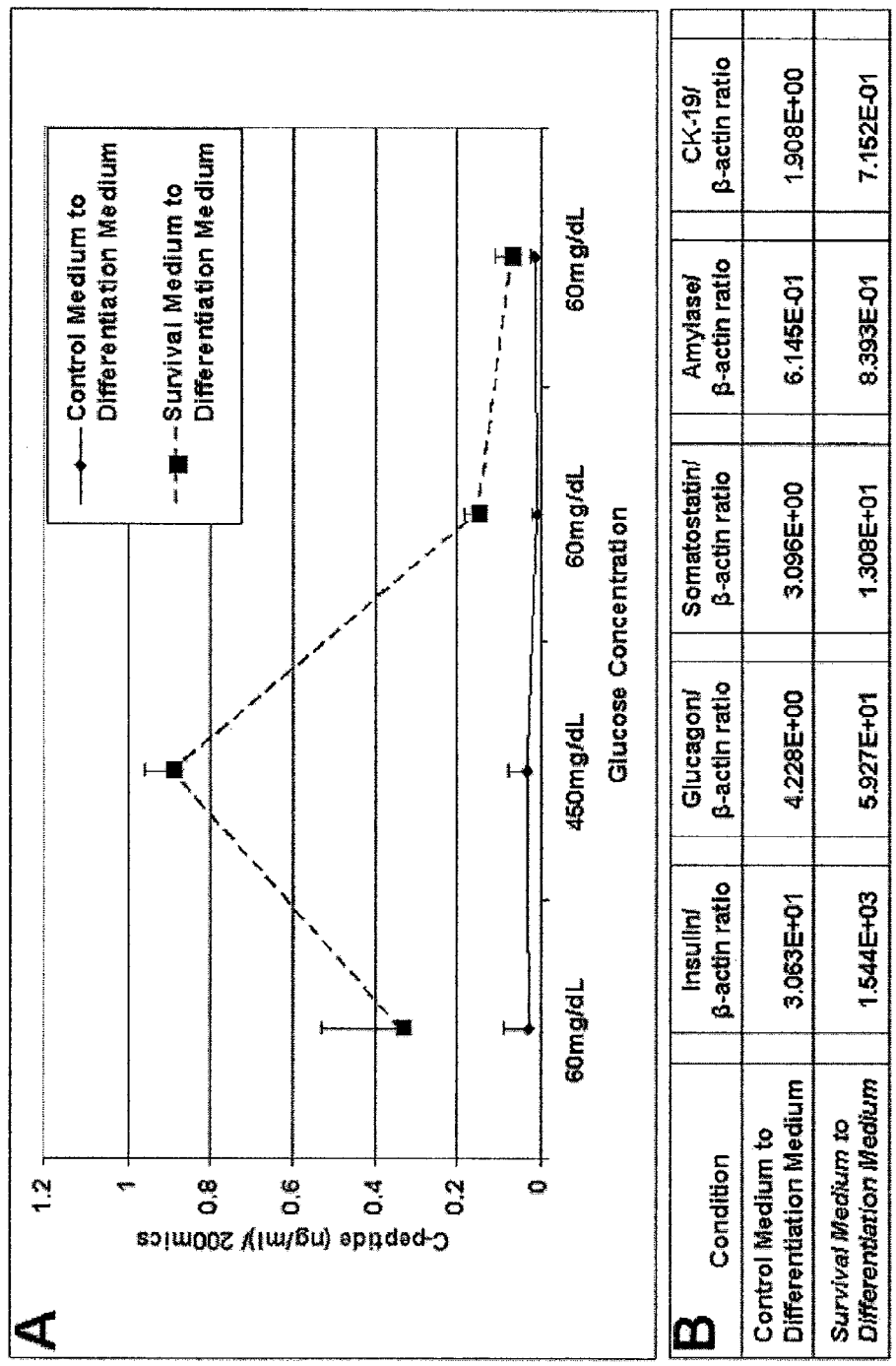

METHOD OF IMPROVING CELL PROLIFERATION OF PANCREATIC PROGENITOR CELLS IN A PANCREATIC CELL CULTURE

CROSS-REFERENCES TO RELATED APPLICATIONS

This application is a 35 U.S.C. §371 filing of International Patent Application No. PCT/US2007/001555, filed Jan. 18, 2007, which claims the priority to U.S. provisional Patent Application No. 60/760,445, filed on Jan. 20, 2006, which is herein incorporated by reference in their entireties.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK.

The content of the following submission on ASCII text file is incorporated herein by reference in its entirety: a computer readable form (CRF) of the Sequence Listing (file name: 596572000600seqlist.txt, date recorded: Aug. 2, 2010, size: 1 KB).

FIELD OF INVENTION

This invention relates to the discovery that Akt, a serine/threonine kinase, is central to the regulation of apoptosis and proliferation in pancreatic endocrine cell cultures. Furthermore, the methods and compositions of the invention allow for improving cell proliferation and survival of pancreatic endocrine cells in a pancreatic cell culture by contacting the cells with, (1) a caspase inhibitor in an amount sufficient to reduce apoptosis in the cells; and, (2) a growth factor in an amount sufficient to increase the level of activated Akt in the pancreatic endocrine cells.

BACKGROUND OF THE INVENTION

The emergence of pancreatic islet transplantation as a means of restoring euglycemia represents a major milestone in the treatment of diabetes. However, the shortage of human donors underscores the importance of developing strategies to proliferate islets in vitro in order to increase the number of islet recipients per donor organ from starting islet preparations. There is evidence in rodents that mature beta cells retain a replicative potential although proliferating human beta cells have not been identified to date (Dor et al., (2004) *Nature* 429 (6897): 41-46). A major thrust in the study of islet proliferation has been the identification of endocrine progenitors that could potentially be expanded exponentially and then driven to express mature endocrine markers, in particular insulin. However, the identity of such progenitors remains to be elucidated.

The loss of islets during the isolation and cell culture process, as well as the loss of functionality in the grafts, is a significant hurdle in achieving sufficient numbers of islets to treat diabetic individuals. Human pancreatic cells cultured in vitro undergo apoptosis leading to a critical loss of endocrine cells. Establishing methods to preserve this material during the various steps prior to transplantation is therefore of critical importance.

During the process of organ procurement and cell isolation, islets are subject to multiple damaging insults resulting from donor brain death, organ isolation and preservation procedures, enzymatic digestion of the pancreas, isolation of the islet fraction, and in vitro cell culture; hence, the requirement for more than one donor pancreas to transplant a single patient. The activation of cell death mechanisms during all these steps is likely to explain the major reduction in functional islet mass observed before and after islet transplantation. This is a substantial constraint limiting the effectiveness of a procedure for the treatment of diabetes.

It is well established that caspases play a major role in the execution of various steps leading to apoptotic cell death. (Chandra, et al., (2001) *Diabetes* 50(supp 1):S44-S47). Inhibition of apoptosis has been shown to contribute to the successful expansion of endocrine cells from the limited number of human pancreas donors available for propagation. (See, e.g., U.S. Pat. No. 6,562,620; Hayek, A. et al., (2002) *Curr. Diab Rep.* 2:371-376). In particular, one approach has been to block the relevant cell death pathways responsible for islet loss and thus enhance the starting islet mass to be transplanted into the patient as disclosed in PCT Intl. Pub. No. WO 200361551. Although inhibition of one or more caspase members can prevent cell death in many cell types, including pancreatic endocrine cells, targeting cell death upstream of caspase cleavage may be more effective.

Several growth factors have been shown to enhance the survival, proliferation and function of islet cells. (Garcia-Ocaña, et al., (2001) *J. Clin. Endocrinol. Metab.* 86:984-988). These growth factors all act upstream of the phosphatidylinositol-3 kinase (P13K) signaling pathway which regulates the survival of various cell types (Stokoe, D. (2005) *Expert Rev. Mol. Med.* 7:1-22; Lin, et al., (1999) *Cancer Research* 59:2891-2897). A key effector of this pathway is the serine/threonine kinase, Akt, which is activated through membrane recruitment and phosphorylation. A role of Akt in the insulin response and in glucose metabolism of various tissues is well documented (Whiteman E. L., et al., (2002) *Trends Endocrinol. Metab.* 10:444-451). For example, mice harboring a deletion of the Akt2 gene exhibit growth deficiencies and are insulin resistant and glucose intolerant. A transgenic mouse expressing constitutively active Akt1 reportedly has both increased beta cell size and total islet mass leading to improved glucose tolerance and complete resistance to experimental diabetes (Tuttle, et al., (2001) *Nat. Med.* 7:1133-1137). Furthermore, recent studies have suggested that constitutive expression of Akt1 by either viral gene transfer or pharmacologic methods improves human islet transplant in diabetic mice (Contreras et al., (2001) *Transplantation* 74:1063-1069; Rao, et al., (2005) *Diabetes* 54:1664-1675).

Ultimately, the goal is to increase islet mass by blocking certain death pathways while simultaneously boosting proliferation and expansion of endocrine cells in order to make islet transplantation a practical approach to treating diabetes. The current invention achieves this goal by providing methods for improving the survival and cell proliferation of pancreatic endocrine cells in a pancreatic cell culture by contacting the cells with, (1) an exogenous caspase inhibitor in an amount sufficient to reduce apoptosis in the cells; and, (2) at least one exogenous growth factor in an amount sufficient to increase the level of activated Akt in the pancreatic endocrine cells. Moreover, the combination of the caspase inhibitors and growth factors provides a synergistic effect not seen in other cell types.

BRIEF SUMMARY OF THE INVENTION

One aspect of the invention provides a method of improving cell proliferation of pancreatic endocrine cells in a pancreatic cell culture by contacting the cells with (1) an exogenous caspase inhibitor in an amount sufficient to reduce apoptosis in the pancreatic endocrine cell; and (2) at least one exogenous growth factor in an amount sufficient to increase the level of activated Akt in the pancreatic endocrine cells.

In some embodiments of the invention, the pancreatic endocrine cells are insulin producing aggregates.

In some embodiment of the invention, the cells are contacted with an exogenous caspase inhibitor. Typical examples of caspase inhibitors that are suitable for use with the invention include Q-VD-OPH, Z-VAD (OMe)-FMK, Ac-VAD-CHO, Boc-D-FMK, BACMK, BI-9B12, Ac-LDESD-CHO, DEVD-CHO and CPP32/Apopain Inhibitor, preferably Q-VD-OPH, Z-VAD (OMe)-FMK.

In some embodiments of the invention, the exogenous caspase inhibitor is present in a concentration range from about 1 µM to about 100 µM, preferably between about 10 to about 100 µM, and more preferably between about 1 to about 10 µM (e.g., 1, 2, 3, 4, 5, 6, 7, 8, 9, 10, 15, 20, 30, 40, 50, 60, 70, 80, 90, and 100 µM).

In another embodiment of the invention, the pancreatic endocrine cells are contacted with an exogenous growth factor sufficient to increase the levels of activated Akt in the cells. Exemplary non-limiting growth factors suitable for use in the invention include PDGF-BB, EGF, IGF-I, IGF-II, and heregulin. In one embodiment, the exogenous growth factors are PDGF-BB, and either IGF-I, and/or IGF-II.

The exogenous growth factors used with the invention are typically present in a concentration range from about 10 ng/ml to about 100 ng/ml of culture medium (e.g., 10, 15, 20, 25, 30, 40, 50, 60, 70, 75, 80, 85, 90, 95, and 100 ng/ml).

Another aspect of the invention is a culture media containing pancreatic endocrine cells. The media comprises an exogenous caspase inhibitor in sufficient amount to reduce apoptosis in the cultured pancreatic endocrine cells. The media further comprises at least one exogenous growth factor in an amount sufficient to increase the levels of activated Akt in the cultured pancreatic endocrine cells.

In some embodiments of the invention, the media contains an exogenous caspase inhibitor. Exemplary non-limiting caspase inhibitors suitable for use with the invention include Q-VD-OPH, Z-VAD (OMe)-FMK, Ac-VAD-CHO, Boc-D-FMK, BACMK, BI-9B12, Ac-LDESD-CHO, DEVD-CHO and CPP32/Apopain Inhibitor. In some embodiments the exogenous caspase inhibitor is Q-VD-OPH, or Z-VAD (OMe)-FMK.

The exogenous caspase inhibitor in the media is typically present in a concentration range from about 1 µM to about 100 µM preferably between about 10 to about 100 µM, and more preferably between about 1 to about 10 µM (e.g., 1, 2, 3, 4, 5, 6, 7, 8, 9, 10, 15, 20, 30, 40, 50, 60, 70, 80, 90, and 100 µM).

In yet another embodiment of the invention, the media contains at least one exogenous growth factor sufficient to increase the levels of activated Akt in the cultured cells. Exemplary growth factors that are suitable for use in the invention include PDGF-BB, EGF, IGF-I, IGF-II, and heregulin. In one embodiment, the exogenous growth factors are PDGF-BB, and either IGF-I, and/or IGF-II.

The exogenous growth factors used with the invention are typically present in a concentration range from about 10 ng/ml to about 100 ng/ml of culture medium (e.g., 10, 15, 20, 25, 30, 40, 50, 60, 70, 75, 80, 85, 90, 95, and 100 ng/ml).

The order in which the pancreatic cells are contacted with the exogenous growth factor and exogenous caspase inhibitor are irrelevant. For example, in some embodiments the cells are contacted with the exogenous caspase inhibitor before being contacted with the exogenous growth factor. In other embodiments the cells are contacted with the exogenous growth factor before being contacted with the exogenous caspase inhibitor. In still other embodiments, the cells are contacted with the exogenous caspase inhibitor and the exogenous growth factor concurrently.

BRIEF DESCRIPTION OF THE DRAWINGS

FIG. 2A shows a quantitative assessment of viability for pancreatic cells prior to passaging as determined by Trypan Blue exclusion staining, represented as a percentage of viable cells over total cell number. FIG. 2B shows C-peptide and Annexin V-EGFP co-staining of human pancreatic cells grown in control medium or survival medium. The center panel shows a control for the specificity of the antibody staining using normal rabbit IgG.

FIG. 3A shows 80% confluent log phase cultures of human pancreatic cells labeled with DAPI (left column) or immunostained with rabbit anti-Ki-67 antibodies (right column). Cell cultures were either grown in control media (top panels) or survival medium (middle panels). Normal rabbit IgG was used as a control for specificity of antibody staining (lower panels). FIG. 3B shows a quantitative assessment of the number of Ki-67 positive cells expressed as a percentage of the total number of DAPI positive cells. FIG. 3C cell number was also calculated by performing cell counts and measuring DNA content in the confluent cultures grown either in control medium or survival medium.

FIG. 4C shows steady state levels of Akt increase upon treatment of cells with survival medium. Immunoblotting was carried out using whole cell lysates from adherent and non-adherent cells grown in either control medium or survival medium and probed with anti-Akt antibodies.

FIG. 8(A-B) show static stimulation and gene expression analysis of encapsulated cells grown in control medium or survival medium and treated with differentiation factors. FIG. 8A Encapsulated cells were evaluated for functionality by sequential incubation in Krebs solutions supplemented with 60mg/dl glucose and 450 mg/dl glucose. Human C-peptide content was quantified using an ultra-sensitive C-peptide ELISA. C-peptide secretion was expressed as accumulation per ml of buffer (A). Cells were recovered from capsules, lysed and subjected to qRT-PCR analysis to determine gene expression shown in FIG. 8B as the ratio of gene to β-actin mRNA. The experiments were done in triplicate and represent an average of two independent experiments.

DETAILED DESCRIPTION OF THE INVENTION

I. Definitions

Figure 1:
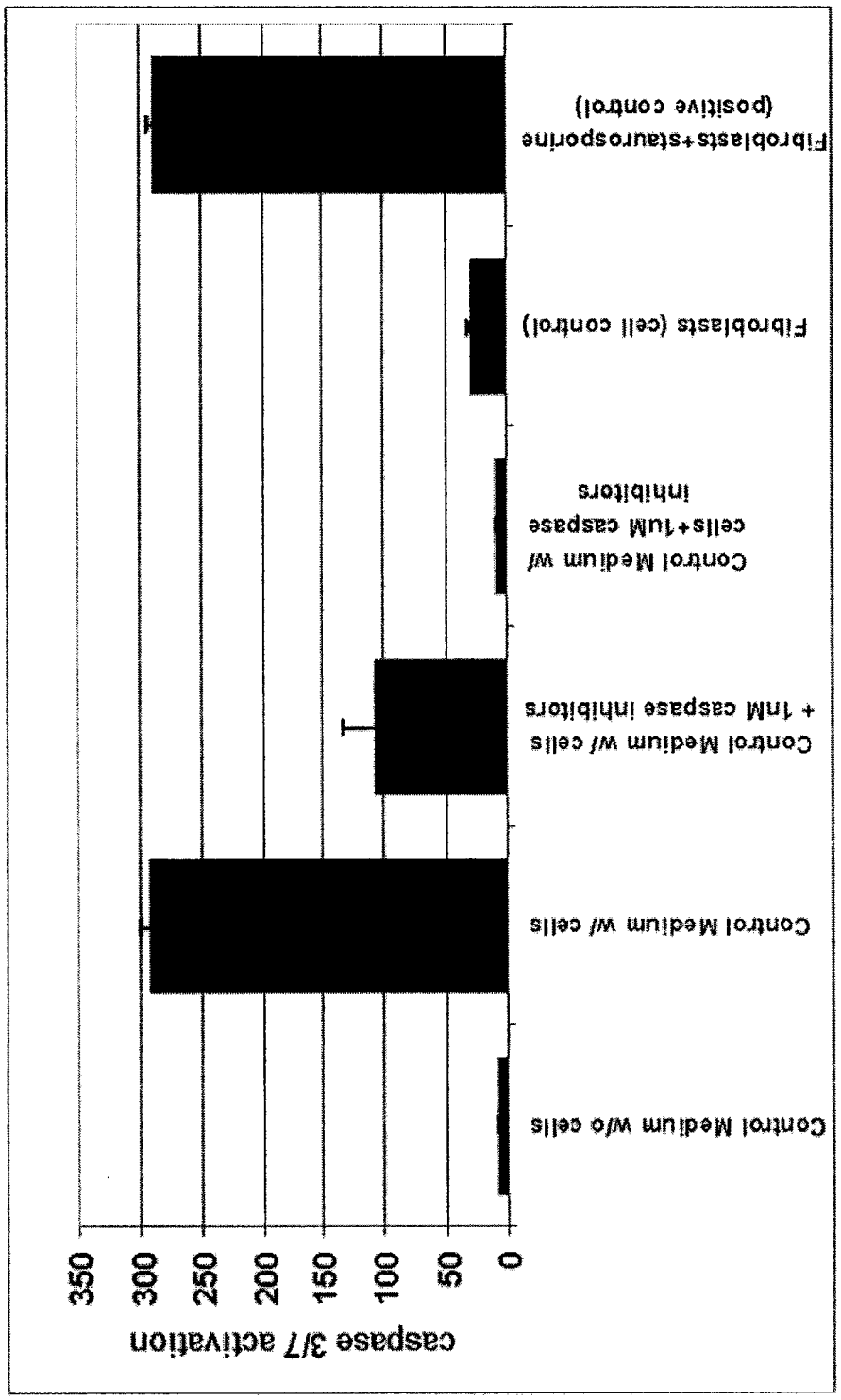
FIG. 1 illustrates that caspases are activated in the human pancreatic cell cultures. To determine the extent of apoptosis as measured by the level of caspase activity in cell lysates of cultured pancreatic cells, a caspase 3/7 colorimetric assay was carried out. As negative and positive controls, caspase activity was measured in cultured human fibroblasts that either received no treatment or were treated with 1 nM staurosporine for 12 hours to induce caspase-dependent apoptosis. A caspase inhibitor, non-O-methylated Q-VD-OPH (OPH-109) was used to show concentration dependence of caspase inhibition. These values are representative of three independent experiments.

Units, prefixes, and symbols are denoted in their Systéme International de Unites (SI) accepted form. Numeric ranges are inclusive of the numbers defining the range. The headings provided herein are not limitations of the various aspects or embodiments of the invention, which can be had by reference to the specification as a whole. Accordingly, the terms defined immediately below are more fully defined by reference to the specification in its entirety. Terms not defined herein have their ordinary meaning as understood by a person of skill in the art.

The term "survival media" as used herein refers to a physiologically acceptable cell culture media containing an exogenous caspase inhibitor in an amount sufficient to reduce apoptosis and at least one exogenous growth factor in an amount sufficient to increase the levels of activated Akt in the cells. Exemplary cell culture media that can be used to make survival media include SM95, F12, DMEM, Eagles MEM, CMRL 1066, RPMI 1640 media, or any combination of these or other physiologically acceptable media, either commercially available or known to persons of skill in the art. The caspase inhibitors may be selective caspase inhibitors, or pan caspase inhibitors. Exemplary caspase inhibitors include Q-VD-OPH, Z-VAD (OMe)-FMK, Ac-VAD-CHO, Boc-D-FMK, BACMK, BI-9B12, Ac-LDESD-CHO, DEVD-CHO CPP32/Apopain Inhibitor. Exemplary growth factors include PDGF-BB, EGF, heregulin, IGF-I and IGF-II.

The term "control media" as used herein refers to a physiologically acceptable cell culture media that does not contain additional exogenous caspase inhibitors in an amount to reduce apoptosis or exogenous growth factors in an amount sufficient to increase the level of full-length, activated Akt in pancreatic endocrine cells.

The term "differentiation media" as used herein refers to a physiologically acceptable cell culture media without FBS, or the Akt stimulators PDGF-BB and IGF in amounts sufficient to increase the levels of activated Akt. Differentiation media does contain other growth factors, cytokines, and chemicals that have been shown to induce differentiation of pancreatic progenitors into mature insulin producing cells. Exemplary differentiation factors include hepatocyte growth factor (HGF), keratinocyte growth factor (KGF), exendin-4, nicotinamide, beta-cellulin and INGAP.

The term "cell proliferation" as used herein refers to the process whereby there is an increase in the number of cells as a result of cell growth and cell division. Cell proliferation is measured by the methods described herein, and may include, but are not limited to, Ki-67 immunolabeling, analysis of DNA content, and cell counts. As used herein, cell proliferation is improved if the levels of cell proliferation in the presence of the exogenous caspase inhibitor and exogenous growth factor is greater than the level of cell proliferation in the absence of the exogenous caspase inhibitor and exogenous growth factor.

The term "pancreatic endocrine cell" as used herein refers to both a mature pancreatic endocrine cell (e.g. an insulin producing aggregate), that expresses markers of a differentiated pancreatic endocrine cell and produces pancreatic hormones (e.g., insulin and glucagon), and a pancreatic progenitor cell that does not express the markers of a differentiated pancreatic cell, and does not produce pancreatic hormones, but is capable of differentiating into a mature pancreatic cell that does express markers of a differentiated pancreatic cell and produces and secretes pancreatic hormones (e.g., insulin and glucagon).

The term "contacting" is used herein interchangeably with for example: combined with, added to, mixed with, passed over, incubated with, flowed over, exposed to, and the like.

The term "exogenous" as used herein refers to any factor or material that is present and active in an individual organism or living cell but that originated outside of that organism or cell.

The term "growth factor" refers to any substance made by an organism, or cells removed from an organism, or produced in the laboratory, that functions to regulate cell division, cell maturation, and or cell survival.

The term "caspase inhibitor" refers to any compound, molecule, or protein that is capable of inhibiting, or reducing the activity of a caspase enzyme.

The term "apoptosis" is used interchangeably with "programmed cell death" and as used herein refers to a type of cell death involving a genetically programmed series of events leading to the death of the cell.

The phrase "exogenous growth factor in an amount sufficient to increase the level of activated Akt" refers to an amount of exogenous growth factor sufficient to produce a detectable increase in the amount of activated Akt as evidenced by western blot analysis of cell homogenates, or other methods as described herein.

The phrase "exogenous caspase inhibitor in an amount sufficient to reduce apoptosis" as used herein refers to an amount of exogenous caspase inhibitor sufficient to show reduced caspase activity, or decreased apoptosis in treated cells as compared to non-treated cells. Reduced caspase activity is determined using a caspase profiling assay, or other methods as described herein, or by other suitable methods known to persons of skill in the art. Apoptosis is detected using annexin-V-EGFP and propidium iodide staining, or other methods as described herein, or other methods known to persons of skill in the art.

The term "activated Akt" as used herein refers to a wild-type, full length member of the Akt protein family, active fragments thereof, or active variants thereof, wherein the fusions retain Akt activity. The Akt protein family includes Akt1, Akt2, and Akt3. The wild-type, full-length Akt proteins are serine/threonine kinases that have a catalytic domain closely related to both PKA and PKC. The term Akt is used interchangeably with RAC protein kinase (related to A and C kinases) and PKB (protein kinase B). Akt family members feature a pleckstrin homology (PH) domain at the amino terminus and a protein serine/threonine kinase catalytic domain at the carboxy terminus.

The term "insulin producing aggregate" as used herein refers to a pancreatic endocrine cell or a collection of pancreatic endocrine cells that produces and secretes insulin.

The term "differentiate" or "differentiation" as used herein refers to a process where cells progress from an undifferentiated state to a differentiated state, or from an immature state to a mature state. For example, undifferentiated pancreatic cells are able to proliferate and express characteristic markers, such as PDX-1. Mature or differentiated pancreatic cells do not proliferate but do secrete high levels of pancreatic endocrine hormones, e.g., mature β cells secrete insulin at high levels. Changes in cell interaction and maturation occur as cells lose markers of undifferentiated cells or gain markers of differentiated cells. Loss or gain of a single marker can indicate that the cell has "matured or differentiated."

The term "differentiation factors" as used herein refers to a compound added to pancreatic cells to enhance their differentiation to mature insulin producing β cells. Exemplary differentiation factors include hepatocyte growth factor, keratinocyte growth factor, exendin-4, basic fibroblast growth factor, insulin-like growth factor-I, nerve growth factor, epidermal growth factor, and platelet-derived growth factor.

The term "cell survival" as used herein refers to the number of cells remaining alive after the occurrence of an event, such as the harvesting, dissociation, and initial culture of cells from an intact organ, as compared to the number of initial cells in the population. As used herein, cell survival is improved if the level of cell survival in the presence of the exogenous caspase inhibitor and exogenous growth factor is greater than the level of cell survival in the absence of the exogenous caspase inhibitor and exogenous growth factor.

The phrase "physiologically acceptable culture medium" as used herein refers to the broth that covers cells in a culture dish, which contains nutrients and supplements required to feed and maintain the cells.

The term "synergistic effect" as used herein refers to the combined effect of an exogenous growth factor and an exogenous caspase inhibitor in improving the proliferation and survival of pancreatic progenitor cells. The synergistic effect is demonstrated by the increased survival and/or proliferation of the pancreatic progenitor cells when contacted by both the exogenous caspase inhibitor and the exogenous growth factor, as compared to the level of survival and/or proliferation as a result of being contacted by each factor alone. The synergistic effect can also be demonstrated in that a lower amount of exogenous growth factor or exogenous caspase inhibitor would be required to achieve the same or similar increase in survival and/or proliferation of pancreatic progenitor cells when compared to the amount of exogenous growth factor and/or exogenous caspase inhibitor needed to achieve the same or similar effect when used alone.

II. Introduction

The emergence of islet transplantation as a means of restoring euglycemia represents a major milestone in the treatment of diabetes. The shortage of human donors, however, underscores the importance of developing strategies to proliferate islets in vitro to increase the number of islet recipients per donor organ from a limited number of starting islet preparations. Therefore, those of skill in the art will recognize that boosting the proliferation and expansion of endocrine cells in culture is necessary if islet transplantation is to become a practical approach for treating diabetes.

It has been noted that during ex vivo cell culture of adult human pancreatic cells using standard methodologies, a large fraction of the cells are non-adherent. Most of these non-adherent cells and many of the adherent cells are lost due to apoptosis using culture methods standard in the art. Many of these cells (both adherent and non-adherent) express gene characteristic of mature endocrine cells or endocrine progenitor cells. Some of these cells, however, can be rescued with in vitro inhibition of caspases. These observations prompted the present inventors to examine the involvement of signaling pathways upstream of caspase activation, including the Akt pathway. It has now been discovered that there is an advantageous interaction between the Akt pathway and the caspase pathway as delineated in pancreatic endocrine cells. Blocking caspase activity in cultures of pancreatic endocrine cells results in reduced apoptosis, as well as increased levels of full-length Akt in the cells, which further contributes to decreased levels of apoptosis in the cells. Surprisingly, it has been discovered that the addition of specific combinations of exogenous growth factors in addition to the addition of exogenous caspase inhibitors has a synergistic effect on enhancing the proliferation and survival of the cultured pancreatic endocrine cells.

This surprising synergy, however, appears to be specific for pancreatic endocrine cells. The combination of an exogenous caspase inhibitor and at least one exogenous Akt activating growth factor (i.e. survival medium) did not show a synergistic effect on the proliferation and survival of hepatic cells cultured using the methods described herein.

Furthermore, it was found that ex vivo culture of adult human pancreatic cells using the methods disclosed herein, reduced the number of non-adherent cells as compared to conventional culture methods. Moreover, the pancreatic endocrine cells cultured by the methods taught herein retain functionality attributed to normal pancreatic endocrine cells. As discussed in more detail below, an increase in pancreatic gene expression (e.g. insulin) in a population of pancreatic endocrine cells, cultured using the methods taught herein as compared to standard methods known in the art, is a direct reflection of the increased proliferation and survival of the pancreatic endocrine cells resulting from the culture methods described herein. Accordingly, the methods as disclosed herein can be used to expand ex vivo the limited numbers of pancreatic endocrine cells, making transplantation of pancreatic islet cells a practical and viable alternative for the treatment of type I diabetes.

III. Isolation of Pancreatic Endocrine Cells

The first step in the practice of the invention is the isolation of pancreatic endocrine cells. Those of skill in the art will recognize that a variety of sources and methods can be used to isolate pancreatic endocrine cells. The methods described herein are not dependent on the age of the donated pancreas. Accordingly, pancreatic material isolated from donors ranging in age from embryos to adults can be used. An exemplary procedure for organ procurement and cell isolation is described in greater detail in Example 1.

A. Isolation of Pancreatic Endocrine Cells from Pancreas

Once a pancreas is harvested from a donor, it is typically processed to yield individual cells or small groups of cells for culturing using a variety of methods. See, U.S. Pat. Nos. 5,830,741 and 5,753,485. One such method calls for the harvested pancreatic tissue to be cleaned and prepared for enzymatic digestion. Enzymatic processing is used to digest the connective tissue so that the parenchyma of the harvested tissue is dissociated into smaller units of pancreatic cellular material. The harvested pancreatic tissue is treated with one or more enzymes to separate pancreatic cellular material, substructures, and individual pancreatic cells from the overall structure of the harvested organ. Collagenase, DNAse, Liberase preparations and other enzymes that are readily available from commercial supplier (Sigma-Aldrich, St. Lois, Mo.; Roche, Indianapolis, Ind.) are contemplated for use with the methods disclosed herein.

Pancreatic tissue, however, once dissociated for culture, can also be used directly in the culture methods of the invention without further separation. Alternatively, isolated source material can be further processed to enrich for one or more desired cell populations. The mixture of cells harvested from the donor source will typically be heterogeneous and thus contain α-cells, β-cells, δ-cells, ductal cells, acinar cells, facultative progenitor cells, and other pancreatic cell types. In some embodiments, the isolated pancreatic cellular material is purified by centrifugation through a density gradient, for example using the methods disclosed in U.S. Pat. No. 5,739,033. A variety of density gradient mediums are suitable for use with the present invention including NYCODENZ®, FICOLL®, or PERCOLL®, which are readily available form commercial suppliers (e.g., Sigma-Aldrich, St. Louis, Mo.).

A typical purification procedure results in the separation of the isolated cellular material into a number of layers or interfaces. Typically, two interfaces are formed. The upper interface is islet-enriched and typically contains 10 to 100% islet cells in suspension. The second interface is typically a mixed population of cells containing islets, acinar cells, and ductal cells. A pellet is formed at the bottom of the gradient, which typically contains primarily (>80%) acinar cells, some entrapped islets, and some ductal cells.

The cellular constituency of the fractions selected for further manipulation will vary for each isolation and will depend in part on which fraction of the gradient is selected for further processing. For example, an enriched population of islet cells can be obtained from an isolated fraction containing at least 10% to 100% islet cells. A skilled artisan will understand that the culture methods described herein can be used with cells isolated from the second interface, from the pellet, or from other fractions or interfaces, depending on the purification gradient used.

IV. Cell Culture and Cultivation of Pancreatic Endocrine Cells and Their Progeny A. General Cell Culture Procedures Once the pancreatic cells are isolated, they are cultured using general cell culture methodology as may be found in Freshney, *Culture of Animal Cells: A Manual of Basic Technique* 4th ed., John Wiley & Sons (2000). Typically, the pancreatic cells are cultured under conditions appropriate to other mammalian cells, e.g., in humidified incubators at 37° C. in an atmosphere of 5% $CO_2$. The pancreatic cells can be cultured on a variety of substrates known in the art, e.g., borosilicate glass tubes, bottles, dishes, cloning rings with negative surface charge, plastic tissue culture dishes, tubes, flasks, multi-well plates, containers with increased growth surface area (GSA), Esophageal Doppler Monitor (EDM) finish, flasks with multiple internal sheets to increase GSA, Fenwal bags, and other culture containers known in the art. Cells may also be grown on culture surfaces pre-coated with defined extracellular matrix components to encourage growth and differentiation of the cells (e.g., fibronectin, Collagen I, Engelbreth-Holm-Swarm matrix, and, preferably, collagen IV or laminin). These and other culture conditions suitable for use with the present invention are known to persons of skill in the art.

Another important factor in the culture of pancreatic cells is the seeding density of the harvested cells, or the a population of cells that has become confluent and is to be transferred to a new substrate. Seeding densities can have an effect on the viability of the cultured pancreatic cells. Optimal seeding densities for a particular culture condition may be determined empirically by seeding the cells at a range of different densities and monitoring the resulting cell survival and proliferation rate. A range of seeding densities has been shown to be effective in producing hormone secreting cells in culture. Typically, cell concentrations range from about $10^2$ to $10^8$ cells per 100 mm culture dish, e.g., $10^2$, $10^3$, $10^4$, $10^5$, $10^6$, $10^7$, or $10^8$ cells per 100 mm culture dish. Cell concentration for other culture vessels may be adjusted by computing the relative substrate surface area and/or medium gas exchange surface area for a different culture vessel (see, Freshney, supra). Cell concentration in terms of culture vessel surface area may be related to cell concentration in terms of media volume by using the appropriate media volume per culture surface area (0.2-0.5 ml/cm² are typical ranges for static culture).

Standard cell culture propagation techniques are suitable for practice of the invention. Briefly, P0 cells are seeded into 100 mm plastic tissue culture dishes at a density of $1\times10^6$ cells. Culture medium is changed every third day and the cells are subcultured to P1 upon reaching 90% confluence, using 0.05% trypsin (trypsin/EDTA, Invitrogen, Carlsbad, Calif.). The split ratio is typically 1:3, but may be as high as 1:6 for cells grown in survival medium. The P1 cultures typically reach 90% confluence in about 3-5 days at which point cells are subcultured to P2 at a ratio of 1:3 for cells grown in control medium and 1:6 for cells grown in survival medium. All subsequent passages were performed as described for the P1 culture. Culture medium is typically changed every three days, or when the pH of the medium indicates that fresh medium is needed.

B. Cell Culture Media

The pancreatic cells of the present invention may be cultured in a variety of media. As described herein, media containing or lacking particular components, e.g. serum, are preferred for certain steps of the isolation and propagation procedures. For example, cells freshly isolated from the pancreas may be maintained in high serum medium to allow the cells to recover from the isolation procedure. Conversely, low serum media favors the selection and propagation of an intermediate stage population. Accordingly, a number of media formulations may be useful in the practice of the invention. The media formulations disclosed here are for exemplary purposes, and non-critical components of the media may be omitted, substituted, varied, or added simply by assaying the effect of the variation on the replication or differentiation of the cell population, using the assays described herein. See, e.g., Stephan et al., *Endocrinology* 140:5841-54 (1999)).

1. Control Media

Culture media usually comprises a basal medium, which is a physiologically acceptable culture medium that includes inorganic salts, buffers, amino acids, vitamins, an energy source, and, in some cases, additional nutrients in the form of organic intermediates and precursors that are involved in protein, nucleic acid, carbohydrate, or lipid metabolism. Exemplary non-limiting basal media suitable for use in the current invention may include F12, Eagle's MEM, Dulbecco's modified MEM (DMEM), RPMI 1640, CMRL 1066, SM95 (the composition of which is shown in Table 1), a 1:1 mixture of F12 and DMEM, and media or combinations thereof known to persons of skill in the art. To support the growth of cells, basal media is usually supplemented with a source of growth factors, other proteins, hormones, and trace elements. These supplements encourage growth, maintenance, and/or differentiation of cells, compensate for impurities or toxins in other medium components, and provide micronutrients lacking in the basal medium. In many culture media, serum is the source of these supplements. Serum can be supplied from a variety of mammalian sources, such as human, bovine, ovine, equine, and the like, and from adult, juvenile, or fetal sources. See Freshney, supra. Fetal bovine serum (FBS) is a commonly used supplement. Concentrations of serum are expressed in terms of volume of serum as a percentage of the total medium volume, and typically range from about 0.1 to 25%, e.g., about 0.1, 0.2, 0.5, 1, 2, 3, 4, 5, 6, 7, 8, 9, 10, 15, 20, or 25%. For some embodiments, the concentration of serum is lowered but not eliminated, and defined or semi-defined supplement mixtures are added to the basal medium. In some applications, the basal medium is supplemented with defined or semi-defined mixtures of growth factors, hormones, and micronutrients, that can be in addition to, or in place of serum. Formulas for such defined media are disclosed herein; others are known in the art or available from commercial sources (see Freshney, supra).

In general, supplemental ingredients added to the culture media described herein may be replaced by natural or synthetic products that have the same biological properties. For example, triiodothyronine, hydrocortisone, and progesterone may all be replaced by natural or synthetic hormones known to activate the same intracellular receptors (thyroid receptors, glucocorticoid receptors, and progesterone receptors). Insulin and EGF are typically human proteins produced by recombinant DNA methodology, but may be replaced by polypeptides purified from natural sources, polypeptides from other species, or by other agonists of the insulin and EGF receptors. Heregulin, a ligand of the ErbB3 receptor, may be replaced by heregulin isoforms and other ErbB3 agonists such as NRG2, NRG3, and NRG4, sensory and motor neuron-derived factor, neurestin, and Ebp-1, heregulin α, heregulin β, heregulin γ, neuregulin-1 and neuregulin-2 (NRG-1 alpha, NRG-1beta, NRG-2 alpha, and NRG-2 beta).

TABLE 1

| SM95 | |
|---|---|
| | Mg/L |
| INORGANIC SALTS | |
| $CaCl_2$ | 78.3 |
| $CuSO_4 \cdot 5H_2O$ | 0.00165 |
| $Fe(NO_3)_3 \cdot 9H_2O$ | 0.025 |
| $FeSO_4 \cdot 7H_2O$ | 0.61 |
| KCl | 271 |
| $MgCl_2$ | 28.36 |
| $MgSO_4$ | 39.06 |
| $KH_2PO_4$ | 34 |
| NaCl | 7262.75 |
| $NaHCO_3$ | 1600 |
| $Na_2HPO_4$ | 101.5 |
| $NaH_2PO_4 \cdot H_2O$ | 31.25 |
| $ZnSO_4 \cdot 7H_2O$ | 0.416 |
| AMINO ACIDS | |
| L-Alanine | 11.225 |
| L-Arginine•HCl | 283.75 |
| L-Asparagine•$H_2O$ | 18.75 |
| L-Aspartic Acid | 16.325 |
| L-Cysteine•$H_2O$ (non-animal) | 43.78 |
| L-Cystine•2HCl | 15.65 |
| L-Glutamic Acid | 18.675 |
| L-Glutamax I | 328.5 |
| Glycine | 89.375 |
| Glycyl-Histidyl-Lysine | 0.000005 |
| L-Histidine HCl•$H_2O$ | 38.69 |
| L-Isoleucine | 31.24 |
| L-Leucine | 42.5 |
| L-Lysine•HCl | 82.125 |
| L-Methionine | 13.12 |
| L-Phenylalanine | 22.74 |
| L-Proline | 43.625 |
| L-Serine | 23.625 |
| L-Threonine | 38.726 |
| L-Tryptophan | 6.51 |
| L-Tyrosine•2$Na_2H_2O$ (non-animal) | 35.9 |
| L-Valine | 38.125 |
| OTHER COMPONENTS | |
| D-Glucose | 3000 |
| HEPES | 1787.25 |
| Na Hypoxanthine | 3.2 |
| Linoleic Acid | 0.066 |
| Lipoic Acid | 0.1525 |
| Phenol Red | 4.675 |
| Na Putrescine•2HCl | 0.191 |
| Na Pyruvate | 137.5 |

TABLE 1-continued

SM95

| | Mg/L |
|---|---|
| VITAMINS | |
| Biotin | 0.037 |
| Ascorbic Acid | 22.5 |
| D-Ca Pantothenate | 1.37 |
| Choline Chloride | 11.49 |
| Folic Acid | 1.826 |
| L-Inositol | 24.3 |
| Niacinamide | 1.03 |
| Pyridoxine•HCl | 1.046 |
| Riboflavin | 0.13 |
| Thiamine•HCl | 1.23 |
| Thymidine | 0.5325 |
| Vitamin $B_{12}$ | 1.04 |
| SUPPLEMENTS | |
| Na Selenous Acid | 0.0034 |
| Epithelial Growth Factor | 0.005 |
| Ethanolamine | 0.03 |
| Phosphoethanolamine | 0.07 |
| Aprotinin | 12.5 |
| Progesterone | 0.0016 |
| Forskolin | 0.205 |
| HeregulinB | 0.004 |
| Bovine Pituitary Extract | 37.5 |
| Hydrocortisone | 0.0923 |
| r.h. insulin | 5.05 |
| $T_3$ | 0.0000015 |
| L-Thyroxine Na | 0.00002 |
| Bovine Transferrin APG | 7.5 |

2. Survival Media

Culture of the isolated pancreatic cells is carried out in a selective medium that promotes the survival and proliferation of the pancreatic endocrine cells. This selective medium, termed herein "survival medium," favors the propagation and survival of cells which retain the ability to secrete pancreatic endocrine hormones, or which retain the potential to mature into differentiated cells which secrete high levels of pancreatic endocrine hormones. In general, survival medium favors the propagation and survival of endocrine or endocrine-like cells at the expense of fibroblasts and mesenchymal cells.

Survival media, as used herein, is comprised of a physiologically acceptable culture media with 0.5-10% fetal bovine serum (FBS) (e.g., 0.5, 1, 2, 3, 4, 5, 6, 7, 8, 9, or 10%) typically 5%. Survival medium also contains an exogenous caspase inhibitor in an amount sufficient to reduce apoptosis in the cultured cells, and at least one exogenous growth factor in an amount sufficient to increase the level of activated Akt in the cultured pancreatic cells. A skilled artisan will understand that the optimal concentration or necessity for a particular supplement may be determined empirically, by changing the concentration of a single ingredient and observing the effect on cell proliferation, survival, and level of activated Akt in the cultured cells using the methods disclosed herein.

The exogenous caspase inhibitor added to the survival media may be either a pan caspase inhibitor or a caspase specific inhibitor both of which are widely available from commercial suppliers (e.g., MP Biomedicals, Solon, Ohio). The caspase inhibitor is typically added at a concentration of about 1 μM to about 100 μM, e.g., 1, 2, 3, 4, 5, 6, 7, 8, 9, 10, 15, 20, 30, 40, 50, 60, 70, 80, 90, or 100 μM. Non-limiting exemplary caspase inhibitors suitable for use with the present invention may include Q-VD-OPH, Z-VAD (OMe)-FMK, Ac-VAD-CHO, Boc-D-FMK, BACMK, BI-9B12, Ac-LDESD-CHO, DEVD-CHO CPP32/Apopain Inhibitor.

At least one exogenous growth factor is added to the survival media in an amount sufficient to increase the level of activated Akt in the cultured cells. Typically, the growth factors are added in a concentration range from about 10 ng/ml to about 100 ng/ml of culture media (e.g., 10, 15, 20, 30, 40, 50, 60, 70, 80, 90, 100 ng/ml of culture media). Non-limiting exemplary growth factors suitable for use with the present invention may include members of the IGF, EGF, and PDGF families. Notably, not all members of any particular family may work. For example, VEGF, which is a member of the PDGF family, did not work with the current invention. A skilled artisan will recognize, however, that growth factors which increase the levels of activated Akt can be readily identified using the assays provided herein.

In accordance with the present invention, pancreatic cells may either be placed directly into survival medium following isolation, or may be transferred to survival medium after being weaned from high serum media to low serum media. Transferring a culture of pancreatic endocrine cells to survival media promotes the proliferation and survival of pancreatic endocrine cells at the expense of fibroblasts and mesenchymal cells. The pancreatic endocrine cell population cultured in survival media maintains high expression levels of pancreatic markers, such as PDX-1, and will continue to show increased levels of proliferation and survival when subcultured in survival medium as compared to cells cultured in control medium. The proliferating cells in the survival media secrete relatively low levels of pancreatic endocrine hormones, such as insulin, but can be differentiated into mature pancreatic endocrine cells that secrete high levels of endocrine hormones, such as insulin, by culturing the cells in differentiation media as described herein. The mature differentiated pancreatic cells do not show enhanced proliferation, and therefore the level of insulin expression in the differentiated cultures is a direct reflection of the increased number of cells as compared to cultures grown in control medium. Details regarding the isolation, culture, and differentiation of pancreatic endocrine cells are given in the Examples.

V. Method of Measuring Cell Proliferation and Survival

A variety of methods for measuring cell proliferation and cell survival are available and known to persons of skill in the art. Non-limiting exemplary methods suitable for measuring cell proliferation and survival in pancreatic endocrine cell cultures may include cell counting using vital dyes or automated cell counters, immunolabeling with proliferation markers, such as Ki-67, and measuring the DNA content of trypsinized cells. These methods are described in more detail in Example 2. Other methods suitable for use with the present invention will be known to persons of skill in the art.

Figure 2:
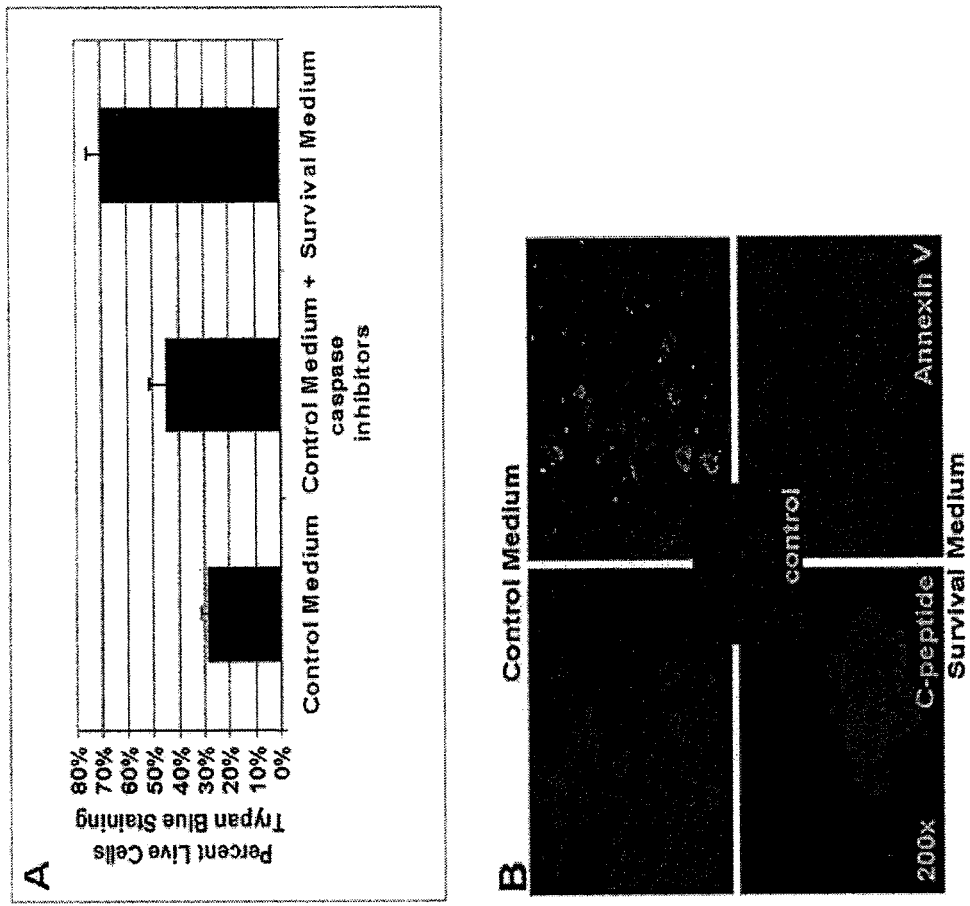
FIGS. 2(A and B) illustrates that Survival Medium rescues human pancreatic cells from apoptosis.

In some embodiments, cell proliferation and survival are measured using the vital dye Trypan Blue (see, e.g., FIG. 2A). Briefly, a single pancreatic cell suspension is generated from a culture that has reached 90% confluency using 0.05% trypsin. A dilution of the trypsinized cells is combined with the vital dye trypan blue. Viable cells exclude the vital dye and are counted under a microscope with the aid of a hematocytometer. The procedure is well known to those of skill in the art and described in Feshney et al.

In other embodiments, the DNA content of the trypsinized cells is measured using a CyQUANT™ cell proliferation assay, according to the manufacturers instructions (Molecular Probes Inc., Eugene Oreg.). The basis of the CyQUANT™ cell proliferation assay is a proprietary green fluorescent dye, CyQUANT GR, which exhibits strong fluorescence when bound to cellular nucleic acids. The assay has a linear detection range extending from 50 cells or fewer to at least 50,000 cells in a 200 µl volume using a single dye concentration (see, e.g., FIG. 3C).

In yet other embodiments, cell proliferation is assessed by immunocytochemical labeling of cultured pancreatic cells with antibodies against the cell proliferation marker Ki-67 (Neomarkers, Fremont, Calif.). See, e.g., FIGS. 3A and B. The immunolabeling is done according to general immunolabeling procedures well known to persons of skill in the art, and described in more detail in Example 2.

VI. Method of Detecting and Measuring Apoptosis

The current invention improves the survival of pancreatic endocrine cell cultures by using caspase inhibitors to reduce apoptosis in the cultures. Persons of skill in the art will recognize that monitoring the levels of apoptosis in the pancreatic endocrine cell cultures is a way of determining when a sufficient amount of caspase inhibitor is present to reduce apoptosis in the pancreatic cell cultures. The methods described below, and in more detail in Example 3, are non-limiting examples of methods used to determine the presence of apoptosis in cell cultures that are suitable for use with the present invention. Additional methods suitable for use with the present invention will be well known to persons of skill in the art.

In some embodiments, the presence of caspases 3 and 7 and the extent of cell death is measured using the APO-ONE™ caspase assay (see, e.g., FIG. 1) according to the manufacturers instructions (Promega Inc., Madison, Wis.).

The detection of early versus late apoptotic cells in pancreatic cell cultures can be determined using Annexin-V-EGFP and propidium iodide (US Biological, Swampscott, Mass.). In the early apoptotic cells, the annexin-V-EGFP will bind phosphatidylserine on the outer membrane of the cell (see, e.g., FIG. 2B) while the late apoptotic cells will take up and retain the propidium iodide. Early and late apoptotic cells can then be quantitated using a fluorescent microscope.

VII. Method of Measuring Increased Level of Full Length Activated Akt Protein

Akt is a key regulator of various insulin-mediated events in pancreatic endocrine cells, including cell proliferation, and survival. In order to improve proliferation in our cultures, growth factors known to stimulate Akt activity are used. One of skill in the art will therefore recognize the importance of monitoring the levels of Akt activity as an indicator of when a sufficient amount of growth factor required to increase the level of activated Akt is present.

The levels of activated Akt protein in the pancreatic endocrine cells can be evaluated using a variety of methods known to persons of skill in the art. Suitable methods for monitoring the levels of activated Akt may include immunocytochemistry, or protein gel electrophoresis and western blotting as shown e.g., in FIG. 4 and described in Example 4. The methods for monitoring the levels of activated Akt can be combined with densitometric analysis, or other suitable methods known to persons of skill in the art, for purposes of quantitating the levels of activated Akt.

VIII. Differentiation-Induction of Insulin Producing Aggregates

Immature pancreatic endocrine cells proliferate and express markers such as PDX-1, while mature pancreatic cells do not proliferate but do secrete high levels of endocrine hormones, such as insulin. Therefore, following expansion of the pancreatic endocrine cells in survival media, it is necessary to differentiate the cells from an immature pancreatic endocrine cells to mature insulin secreting cells that can be used in islet transplantation. A variety of methods and differentiation factors known in the art are suitable for use with the present invention to enhance the differentiation of pancreatic endocrine cells into mature insulin secreting cells as described below.

Differentiation of the pancreatic endocrine cells can be induced through the induction of cell aggregation, which can be induced in a variety of ways. For example, aggregation and differentiation can be induced by growing cells on conditioned culture dishes. For example, in some embodiments, plates conditioned with collagen coating are used to induce aggregation and differentiation of pancreatic endocrine cells.

Alternatively, aggregation and differentiation can be induced by growing the cells to confluence, or treating the cells with differentiation media (DM). Differentiation media is a physiologically acceptable culture media without FBS and without Akt stimulators such as PDGF-BB or IGF. Differentiation media, however, does contain a variety of other growth and differentiation factors that do not stimulate Akt, or are present in levels insufficient to stimulate Akt. Non-limiting exemplary differentiation factors may include hepatocyte growth factor, keratinocyte growth factor, exendin-4, nicotinamide, beta-cellulin, INGAP, b-FGF, NGF EGF, IGF-1, and PDGF. Hepatocyte growth factor has been shown to effect differentiation of pancreatic cells in culture and in transgenic animals. See e.g., Mashima, H. et al., *Endocrinology*, 137:3969-3976 (1996); Garcia-Ocana, A. et al., *J. Biol. Chem.* 275:1226-1232 (2000); and Gahr, S. et al., *J. Mol. Endocrinol.* 28:99-110 (2002). Keratinocyte growth factor has been shown to effect differentiation of pancreatic cells in transgenic animals. See e.g., Krakowski, M. L., et al., *Am. J. Path.* 154:683-691 (1999) and Krakowski, M. L., et al., *J. Endocrinol.* 162:167-175 (1999). Exendin-4 has been shown to effect differentiation of pancreatic cells in culture. See e.g., Doyle M. E. and Egan J. M., *Recent Prog. Horm. Res.* 56:377-399 (2001) and Goke, R., et al., *J. Biol. Chem.* 268:19650-19655 (1993). Basic FGF, (bFGF), has been shown to increase the insulin secretion in microencapsulated pancreatic islets. See e.g., Wang W., et al., *Cell Transplant* 10(4-5): 465-471 (2001). IGF-I has an effect on differentiation of pancreatic ductal cells and IGF-I replacement therapy has been used for type I diabetes treatment. See e.g., Smith F E., et al., *Proc. Natl. Acad. Sci. USA.* 15;88(14): 6152-6156 (1991), Thrailkill K M. et al., *Diabetes Technol. Ther.* 2(1): 69-80 (2000). Evidence has shown that NGF plays an important autoregulatory role in pancreatic beta-cell function. See e.g. Rosenbaum T. et al., *Diabetes* 50(8): 1755-1762 (2001), Vidaltamayo R. et al., *FASEB* 16(8): 891-892 (2002), and Pierucci D. et al., *Diabetologia* 44(10): 1281-1295 (2001). EGF has been shown to promote islet growth and stimulate insulin secretion. See e.g., Chatterjee A K. et al., *Horm. Metab. Res.* 18(12): 873-874 (1986). Additional differentiation factors suitable for use with the present invention will be known to persons of skill in the art.

IX. Characterization of Pancreatic Endocrine Cells and Their Progeny

Those of skill in the art will recognize that it is useful to determine the differentiation state of the pancreatic endocrine cells and their progeny at particular stages of the culture to determine if mature pancreatic endocrine cells are present. The differentiation state of pancreatic cells can be determined in a variety of ways, including measurement of protein and mRNA markers (e.g., PDX-1 or insulin) and functional assays, e.g. ability to secrete insulin in response to glucose stimulation. See, e.g. FIGS. 6 and 8 respectively.

A. Phenotypic Assays

To know when mature pancreatic cells are present, it is useful to assay the phenotypes of pancreatic endocrine cells at particular stages of culture. Since expression of particular proteins correlates with cell identity or differentiation state, cells may be analyzed for the expression of a marker gene or protein to assess their identity or differentiation state. For example, in freshly isolated pancreatic tissue, expression of amylase identifies the cell as an exocrine acinar cell, while expression of insulin identifies the cell as an endocrine islet cell. Likewise, islet cells at an early stage of differentiation are usually positive for the cytokeratin CK-19, while mature islet cells show less expression of CK-19.

Phenotypic properties may be assayed on a cell-by-cell basis or as a population average. The mode of assay will depend on the particular requirements and methodology of the assay technique. Thus, assays of marker expression by immunohistochemistry, performed on fixed sections, or on suspended cells by FACS analysis, measure the frequency and intensity with which individual cells express a given marker. On the other hand, it may be desirable to measure properties such as the average insulin to actin mRNA expression ratio over an entire population of cells. In such cases, the assay is typically performed by collecting mRNA from a pool of cells and measuring the total abundance of insulin and actin messages (see, e.g., FIGS. 6 and 8B). Many phenotypic properties may be assayed either on a cell or population basis. For example, insulin expression may be assayed either by staining individual cells for the presence of insulin in secretory granules, or by lysing a pool of cells and assaying for total insulin protein. Similarly, mRNA abundance may be measured over a population of cells by lysing the cells and collecting the mRNA, or on an individual cell basis by in situ hybridization.

Figure 7:
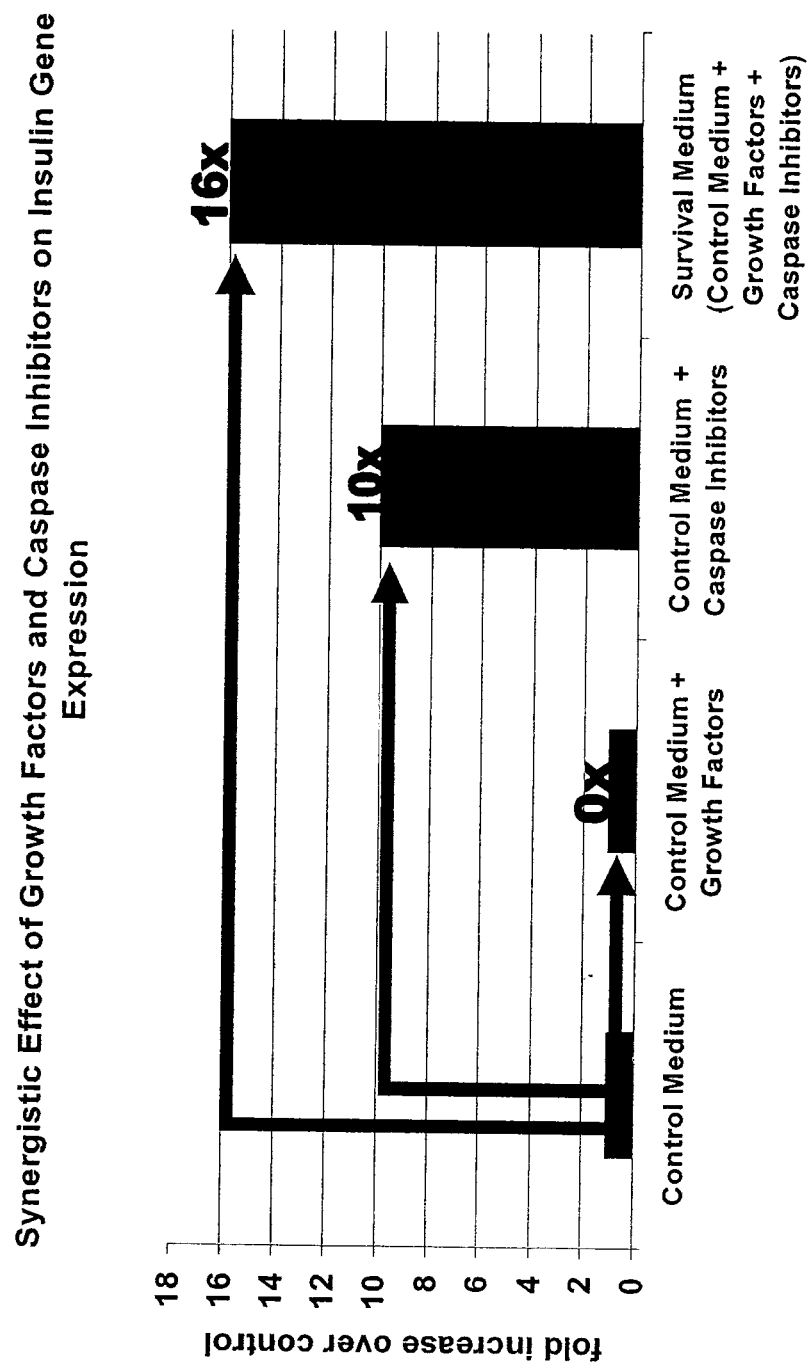
FIG. 7 illustrates synergy between the Akt activating growth factors and a caspase inhibitor on insulin gene expression in the pancreatic endocrine cultures. The data is the ratio of insulin mRNA normalized to β-actin mRNA expressed as fold increase over the ratio obtained from growth of cells in control media alone. The results show that Akt activating growth factors added to the control media have no effect on increasing insulin gene expression over that of cells grown in control media alone. This indicates that growth factors alone do not increase the proliferation or survival of the endocrine cell population. The addition of a caspase inhibitor (OPH-109) however, results in a 10-fold increase in insulin gene expression over that of cells grown in control media alone. This indicates reduced apoptosis and increased survival of the endocrine cell population. Surprisingly, the combined effect of Akt activating growth factors and caspase inhibitor in control media (i.e. survival media) acts synergistically to increase the insulin gene expression 16-fold over that of cells grown in control media alone. This synergy indicates an increased proliferation and survival of the endocrine population over that seen in the presence of either growth factor or caspase inhibitor alone as compared to control media.

As noted previously, because mature pancreatic endocrine cells do not proliferate, an increase in the level of mature markers (e.g., insulin) is indicative of an increase in the number of mature insulin secreting cells, reflecting an increase in the proliferation and/or survival of the endocrine cell population. A synergistic effect on insulin expression, and hence the proliferation and survival of the mature pancreatic endocrine cell population is seen with the combined treatment of caspase inhibitors and Akt activating growth factors present in the survival medium. This synergistic effect is clearly shown in FIG. 7. As can be seen in the figure, the addition of Akt activating growth factors alone does not result in an increase in the insulin/β-actin mRNA ratio compared to cells grown in control media alone. This indicates that the exogenous growth factors alone are not sufficient to increase the proliferation and/or survival of the endocrine cell population. Addition of a caspase inhibitor, such as OPH-109, to the control media, however, results in a 10-fold increase in insulin/β-actin mRNA ratio over that of cells grown in control media alone. This indicates that endocrine cells normally destined to undergo apoptosis in the control media are rescued and survive following addition of the caspase inhibitor. Surprisingly, the addition of both the Akt activating growth factors and the caspase inhibitor to the control media (i.e. survival media) creates a synergy resulting in a 16-fold increase in the insulin/β-actin mRNA ration over that of control media alone. This synergy is due to the proliferation of the endocrine cell population that was rescued from apoptosis by the caspase inhibitor.

1. Cell Differentiation Markers

Various populations of endocrine cells and different stages of differentiation can be identified based on expression of various cellular markers known in the art. Upon isolation and culture, donor pancreatic endocrine cells begin to display various phenotypic and genotypic indicia of differentiated pancreatic endocrine cells. The phenotypic and genotypic indicia of the various cell populations and stages of differentiation include numerous molecular markers present in the facultative progenitor cell population that are modulated (e.g., either up or down regulated) during the culture process.

Developmental stages can be determined by identifying the presence or absence of specific markers in developing cells. Because human endocrine cells develop in a similar manner, various markers can be used to identify cells as they transition from the pancreatic endocrine progenitor cells to the mature insulin producing aggregate phenotype.

The expression of markers in cells induced to proliferate or differentiate by the methods of the present invention bears some similarity to the sequence of marker expression in normal human pancreas development. The markers of interest are molecules that are expressed in temporal- and tissue-specific patterns in the pancreas (see e.g., Hollingsworth, *Ann NY Acad Sci* 880:38-49 (1999)). These molecular markers are divided into three general categories: transcription factors, notch pathway markers, and intermediate filament markers. Examples of transcription factor markers include PDX-1, NeuroD, Nkx-6.1, Isl-1, Pax-6, Pax-4, Ngn-3, and HES-1. Examples of notch pathway markers include Notch1, Notch2, Notch3, Notch4, Jagged 1, Jagged2, Dll1, and RBPjk. Examples of intermediate filament markers include CK19 and nestin. Examples of markers of precursors of pancreatic β cells include PDX-1, Pax-4, Ngn-3, and Hb9. Examples of markers of mature pancreatic β cells include insulin, somatostatin, glp-9, and glucagon.

2. General Methods for Assessing Pancreatic Cell Phenotype

Methods for assessing expression of protein and nucleic acid markers in cultured or isolated cells are standard in the art and include quantitative reverse transcription polymerase chain reaction (RT-PCR), northern blots, in situ hybridization (see e.g., *Current Protocols in Molecular Biology* (Ausubel et al., eds. 2001 supplement)), immunoassays, such as immunohistochemical analysis of sectioned material, western blotting, and for markers that are accessible in intact cells flow cytometry analysis (FACS) (see e.g., Harlow and Lane, *Using Antibodies: A Laboratory Manual*, New York: Cold Spring Harbor Laboratory Press (1998)). Conventional histochemical markers of endocrine cell differentiation may also be employed. Cells to be examined by immunohistochemistry or immunofluorescence may be cultured on glass chamber slides for microscopic examination. See, Harlow and Lane, supra. Alternatively, cells grown in conventional tissue culture dishes may be manually removed from the culture and embedded in paraffin for sectioning. PDX-1 antibody can be made following the teachings of Leonard J. et al., Mol. Endocrinol., 10:1275-1283 (1993) or purchased from commercial suppliers such as Incstar, Inc. (Stillwater, Minn.). Specific methods for analyzing the phenotype of pancreatic endocrine cells are detailed more fully in Example 5.

B. Functional Assays

One of the important functions of a beta cell proliferated and expanded by the methods described herein, is to adjust its insulin secretion according to the glucose level. Typically, a static glucose stimulation (SGS) assay can be performed on the proliferating adherent pancreatic cells to identify whether they are able to secrete insulin in response to different glucose levels. Cells are generally cultured on an appropriate substrate until nearly confluent. One to three days prior to the SGS test, the culture medium is replaced by a medium of similar character but lacking insulin and containing only 1 g/L of glucose. The medium is changed each day and the SGS test is performed on day four as described in Example 6.

X. Encapsulation and Implantation

Encapsulation of pancreatic endocrine cells results in the formation of cellular aggregates in the capsules. Encapsulation can allow the pancreatic cells to be transplanted into a diabetic host, while minimizing the immune response of the host animal. It also allows the further maturation of pancreatic progenitors in a three-dimensional environment. The porosity of the encapsulation membrane can be selected to allow secretion of biomaterials, like insulin, from the capsule, while limiting access of the host's immune system to the foreign cells.

Encapsulation methods are known in the art and are disclosed in, for example, the following references: van Schelfgaarde & de Vos, *J. Mol. Med.* 77:199-205 (1999), Uludag et al. *Adv. Drug Del Rev.* 42:29-64 (2000) and U.S. Pat. Nos. 5,762,959; 5,550,178; and 5,578,314. Encapsulation methods are also described in detail in international application PCT/US02/41616; incorporated herein by reference.

Implantation or transplantation into a mammal and subsequent monitoring of endocrine function may be carried out according to methods commonly employed for islet transplantation. See, e.g., Ryan et al., *Diabetes* 50:710-19 (2001); Peck et al., *Ann Med* 33:186-92 (2001); Shapiro et al., *N Engl J Med* 343(4):230-8 (2000); Carlsson et al., *Ups J Med Sci* 105(2):107-23 (2000) and Kuhtreiber, W M, Cell Encapsulation Technology and Therapeutics, Birkhauser, Boston, 1999. Non-limiting exemplary sites for implantation include subcutaneous sites and sites within the peritoneal cavity, such as the omental pouch.

One of skill in the art will be able to determine an appropriate dosage of microcapsules for an intended recipient, and will depend on the insulin requirements of the recipient. Insulin levels secreted by the microcapsules can be determined by numerous methods known in the art, e.g., immunologically or by amount of biological activity. The recipient's body weight can also be taken into account when determining the dosage. If necessary, more than one implantation can be performed as the recipient's response to the encapsulated cells is monitored. Thus, the response to implantation can be used as a guide for the dosage of encapsulated cells (see Ryan et al., *Diabetes* 50:710-19 (2001)).

The function of encapsulated cells in a recipient can be determined by monitoring the response of the recipient to glucose. Implantation of the encapsulated cells can result in control of blood glucose levels. In addition, evidence of increased levels of C-peptide, or pancreatic endocrine hormones such as insulin, glucagon, and somatostatin are also indicative of function of the transplanted encapsulated cells.

One of skill in the art will recognize that control of blood glucose can be monitored in different ways. For example, blood glucose can be measured directly, as can body weight and insulin requirements. Oral glucose tolerance tests can also be given. Renal function can also be determined as can other metabolic parameters. (Soon-Shiong, P. et al., *PNAS USA* 90:5843-5847 (1993); Soon-Shiong, P. et al., *Lancet* 343:950-951 (1994)).

All patents, patent applications, and other publications cited in this application are hereby incorporated by reference in their entirety for all purposes.

EXAMPLES

The following examples are included for illustration purposes and are not intended to be construed as a limitation on the invention in any way. It should be appreciated by those of skill in the art that the techniques disclosed in the examples which follow represent techniques discovered by the inventor to function well in the practice of the invention, and can thus be considered to represent preferred modes for practice of the invention. However, those skilled in the art should, in light of the present disclosure, appreciate that many changes can be made in the specific embodiments disclosed and still obtain similar results without departing from the spirit or scope of the invention.

Example 1

Pancreatic Endocrine Cell Culture

A. Organ Procurement

Pancreatic cells are isolated from cadaver pancreases. Organ harvesting is orchestrated by United Network for Organ Sharing ("UNOS") and local organ donor organizations. Only donors with signed consent forms for research are used.

For harvesting the pancreas, the abdominal aorta is cannulated below the junction of the renal artery, and the portal perfusion is cannulated via the inferior mesentery vein. The cannula is inserted into the portal vein (PV) to the level above the junction of the splenic vein (SV) to the PV. A loose 2-0 tie is put around the SV at the junction with the portal vein, and another loose 2-0 tie is put around the splenic artery (SA). The SV tie is ligated and cut open on the spleen side immediately before the perfusion starts. This makes the pancreas perfusion more efficient without aortic/portal double end pressure which may damage the islets. It also allows all the portal perfusant to go into the liver and avoids draining the perfusant from the spleen and pancreas into the liver. The lesser sac is opened and a normal saline ("NS") slush is applied over the pancreas. After 1 L of aorta perfusion, the SA is ligated. The pancreas should be well protected when the liver and kidneys are harvested. The pancreas is retrieved with the procedures known and used in the art for pancreas transplants.

The organ is stored in a plastic bag filled with "Belzer solution," a cold storage solution for organ preservation. See, e.g., Uhlmann et al., *J Surg Res.* 105(2):173-80 (2002). Belzer UW solution is also commercially available under the name VIASPAN® (Barr Laboratories, Inc., Pomona, N.Y.).

B. Pancreas Digestion

The islets are isolated by enzymatic pancreas digestion. One vial of Liberase (0.5 g, Roche) is dissolved in 333 ml of HBSS (1.5 mg/ml, 37° C.) and infused into the pancreas via ductal cannulation(s). The organ is incubated in an 800 ml tempering beaker at 37° C. for 10~20 minutes until the tissue becomes soft.

The semi-digested tissue mass is transferred into the metal digestion chamber and automatic circulating digestion started. Tissue is dissociated by agitation of the digestion chamber.

When the majority of islets have been released from the surrounding tissue, the digestant is collected and diluted with Medium A10 (10% fetal bovine serum in RPMI). The digestion procedure takes about 30 minutes. The cells are washed with A10 three times at 4° C., 1,000 rpm, 2 minutes, and then go through the cell separation procedure.

C. Pancreatic Cell Separation

The pellet resulting from the washing and centrifugation procedure described in the preceding paragraph is mixed with 320 ml Pancreatic Islet Purification Solution ("PIPS") (a 13.7% solution of NYCODENZ® AG (Axis-Shield PoC AS, Oslo, Norway; NYCODENZ® is a centrifuge density gradient solution with the systemic name 5-(N-2,3-dihyroxypropylacetamide)-2,4,6-tri-iodo-N,N'-bis(2,3 dihydroxypropyl)isophtalamide) prepared in VIASPAN® Belzer UW solution (density 1.114) and set on ice for 10 minutes.

Each of eight 250 ml flat-bottom centrifuge tubes are filled with 70 ml PIPS (density 1.090). Forty ml of cell/PIPS suspension is then under-laid into each tube. Sixty ml of RPMI 1640 with 2% FBS is over-laid on top of the PIPS. The tubes are centrifuged for six minutes without braking, using a Sorvall RC-3C Plus with a 05, ARC rotor at 1,500 rpm.

The upper interface (A layer, purified islets), lower interface (B layer, mixture of entrapped islets, fragmental islets, acinar and ductal cells) and the pellet (mainly acinar and ductal cells) are collected separately. The cells are washed two more times with Medium A10 and then used as desired.

D. Pancreatic Cell Culture

Pancreatic cells were seeded into 100 mm plastic tissue culture dishes (BD Biosciences, San Jose, Calif.) at a concentration of $1 \times 10^6$ cells/ml in either 10 ml SM95/RPMI 1640 with 5% FBS (1:1 ratio, designated as control media), or a mixture of SM95/RPMI 1640 (1:1 ratio) medium with 5% FBS with the following supplements: exogenous growth factors rhPDGF-BB (70 ng/ml), rhIGF-I (50 ng/ml), and rhIGF-II (50 ng/ml) (all from R&D Systems Inc.), and an exogenous caspase inhibitor non-O-methylated VD-OPH (100 μM) (MP Biomedical, Solon, Ohio) (designated as survival media). Culture medium was changed every third day and the cells were subcultured to P1 upon reaching 90% confluence, using 0.05% trypsin (trypsin/EDTA, Invitrogen, Carlsbad, Calif.), at a split ratio of 1:4 for cells in control media and 1:6 for cells in survival media. P1 cultures reached 90% confluence in about 5 days at which point cells were subcultured to P2 at a split ratio of 1:3. All subsequent passages were performed as described for the P1 cultures.

Example 2

Proliferation of Pancreatic Endocrine Cells Grown in Survival Media

A. Counting of Viable Cells Using Trypan Blue

To assess proliferation and survival of pancreatic endocrine cells cultured in survival media compared to culture in control media, cell numbers and proliferation were assessed during the different stages of the culture process. Upon reaching 90% confluence, a single pancreatic cell suspension was generated using 0.05% trypsin. Using trypan blue for viability assessment, viable cells were counted using a hematocytometer. Results indicated an increased number of viable cells in cultures treated with survival media as compared to cultures treated with control media.

B. Immunolabeling with Antibodies Against the Cell Proliferation Marker, Ki-67

Pancreatic endocrine cells grown and expanded in survival media proliferate and survive at a greater rate than pancreatic endocrine cells grown and expanded in control media. To confirm this, cells were grown in 4-well chamber slides and fixed in 4% paraformaldehyde at room temperature. Cells were incubated in blocking buffer (PBS/3% BSA/1% normal goat serum) for 1 hour then permeabilized with PBS/0.2% TritonX for 5 minutes. Cells were then washed with blocking buffer, and incubated with a polyclonal guinea pig anti-human C-peptide antibody (DAKO Inc., Carpinteria, Calif.) or a rabbit anti-Ki-67 antibody (Neomarkers, Fremont, Calif.) for 1 hour at room temperature. Cells were then washed three times for 15 minutes each with PBS/1% TritonX/1% BSA and incubated in secondary Alexafluor 488 conjugated antibody (Molecular Probes, Eugene, Oreg.) for 1 hour. Cells were then washed three times for 15 minutes each and again fixed in 4% paraformaldehyde. Cells were then washed in PBS/RNAse for 5 minutes, and mounted with Vectashield containing DAPI nuclear stain (Vector Labs, Burlingame, Calif.). FIG. 3A shows pancreatic cells grown in either control or survival media immunolabeled with Ki-67 as described above. The results indicated that on average there was approximately a 5-fold greater Ki-67 labeling of the cells grown in survival media as compared to cells grown in control media (see FIG. 3B).

C. DNA Content as an Indicator of Cell Proliferation.

The increased cell number indicated by the Ki-67 labeling was confirmed by measuring the DNA content of the trypsinized cells using the CYQUANT cell proliferation assay (Molecular Probes, Inc. Eugene, Oreg.), according to the manufacturer's instructions. Cells were lysed by addition of a buffer containing the CYQUANT GR dye. A fluorescence microplate reader was then used to directly measure the fluorescence of the samples. The assay has a linear detection range extending from 50 to 50,000 cells in a 200 μl volume using a single dye concentration. Results of cells not in log phase showed a higher DNA content, and thus greater cell number, by approximately 30% when grown in survival medium as compared to growth in control medium (see, FIG. 3C).

Example 3

Detection of Apoptosis and Active Caspases in Pancreatic and Fibroblast Cell Cultures A. Apoptosis in Pancreatic and Fibroblast Cell Cultures.

One of the earliest indications of apoptosis is the translocation of the membrane phospholipid phosphatidylserine (PS) from the inner to the outer leaflet of the plasma membrane. Once PS is exposed to the extracellular environment, its binding sites become available for Annexin V, a 35-36 kDa, Ca 2+-dependent, phospholipid binding protein with a high affinity for PS. For determination of cells undergoing early apoptosis, P0 pancreatic cells, or normal cycling human fibroblasts, were plated on 4-well chamber slides and grown under conditions described herein. Prior to being passaged, the cells were incubated with a fluorescent conjugate of Annexing V, annexin-V-EGFP, in 500 ml μl binding Buffer for 5 minutes per the manufacturer's instructions (U.S. Biological, Swampscott, Mass.). The apoptotic cells were visualized and counted utilizing a fluorescence microscope using a dual filter for FITC and rhodamine, respectively. The pancreatic cells stained positive for annexin-V, as compared to the normal cycling fibroblasts which did not stain. We determined that the annexin-V staining of the P0 pancreatic cells was specific because annexin-V binding is calcium dependent and addition of 1 uM EGTA, a calcium chelator (Sigma, St Louis, Mo.) to the P0 pancreatic cultures as a control, abolished the staining.

Among the cells being lost were beta-cells and putative endocrine progenitors as indicated by the PDX-1, Ngn3, NeuroD and insulin mRNA profiles of the adherent and non-adherent populations. In addition, dual label immunofluorescence with anti-human C-peptide (DAKO, Carpinteria, Calif.) at a 1:1000dilution and annexin-V revealed that many of the beta cells (anti-human C-peptide positive) were also annexin-V positive (see FIG. 2B). These results indicated that in vitro cell culture of human pancreatic cells results in the loss of valuable endocrine lineage cells to apoptosis.

B. Effect of Caspase Inhibitors on Caspase Activation in Pancreatic Endocrine Cells and Fibroblast Cultures.

One of the hallmarks of apoptosis is caspase activation. The downstream caspases 3 and 7 have a consensus cleavage sequence DEVD (SEQ ID NO: 1). For determination of the extent of apoptosis in our cultures, we used the Apo-ONE assay system (Promega), according to the manufacturer's instructions (FIG. 1). Cells were plated on 96 well plates, and cell lysates were prepared in a buffer that supports caspase activity (Promega, Madison, Wis.) and analyzed on a fluorescent plate reader using the Apo-ONE caspase 3/7 fluorescent assay (Promega, Madison, Wis.) at an excitation wavelength was 485 run and an emission wavelength was 530 nm. Our analysis showed that caspases were activated in pancreatic cells from P0 cultures from adherent cells at a level comparable to levels in fibroblast cultures treated with staurosporine, a potent inducer of apoptosis and caspase activity. The addition of a broad range caspase inhibitor, VD-OPH-19, (MP Biomedicals, Solon, Ohio.) at a concentration of 1 µM completely reversed the caspase activation observed (see FIG. 1).

Example 4

Determination of Activated Akt Levels Using Gel Electrophoresis and Western Blotting To assess the effects of our pancreatic cell culture conditions on levels of Akt, we measured the steady state levels of Akt protein by western blot analysis (FIGS. 4A and B). After three days in culture and one media change, we collected both adherent and non-adherent fractions from the pancreatic cell cultures for gel electrophoresis and immunoblot analysis. As controls, we examined human primary fibroblasts that were either treated with staurosporine (a potent inducer of apoptosis and caspase activity) as a positive control for apoptosis, or not treated as a negative control. Cell monolayers and suspensions were washed twice with cold PBS and lysed at 4° C. in RIPA buffer (50 mM Tris-HCL pH 7.4, 1% NP-40, 150 mM NaCl, 0.25% Na-deoxycholate, 1 mM EDTA, 1 mM PMSF, 1 mM β-glycerophosphate and 1 mM NaF) containing a cocktail of protease inhibitors (Roche, Palo Alto). Cell lysates were centrifuged at 4° C. to remove debris, and the protein concentration was determined for each supernatant by using the BIORAD Protein Assay reagent (Biorad) as indicated by the manufacturer. An equal volume of 2× Laemmli SDS sample buffer was added to each sample. Samples were boiled and equal amounts of protein were loaded onto the gel. Proteins were separated by SDS-PAGE and transferred onto PVDF membranes. Western blot analysis was carried out by blocking the membranes in PBS containing 3% non-fat dry milk buffer for 2 hours at room temperature. Gel electrophoresis and western blotting was carried out as described above, with the exception that for the membranes probed with phosphospecific antibodies, the blocking buffer was PBS with 3% BSA. Blots were probed with antibodies diluted 1:100 against Akt, and phospho-serine 473-Akt (Cell Signaling, Beverly, Mass.). An antibody against GAPDH (Santa Cruz) was used at a 1:500 dilution as a loading control. Blots were subsequently incubated in secondary HRP-conjugated antibodies diluted 1:15,000 (Pierce). Detection of proteins was performed using enhanced chemiluminescence (ECL) (Pierce). Immunoblot analysis with Akt antibodies revealed cleavage of full length Akt in non-adherent cells and the presence of a number of proteolytic fragments that were also apparent to a lesser extent in the adherent cell fractions. This phenomenon was not apparent in primary fibroblasts treated with staurosporine, a potent inducer of apoptosis, and hence represent a novel mechanism of Akt inactivation. Furthermore, the presence of Akt cleavage even in adherent cells indicates that such cells are destined for apoptotic cell death, consistent with earlier findings that numerous adherent cells also stain positive for Annexin V. Addition of Akt activating growth factors resulted in elevation of steady state levels of Akt (FIG. 4C) and established a correlation between improved cell viability and an increase in Akt protein.

Figure 4:
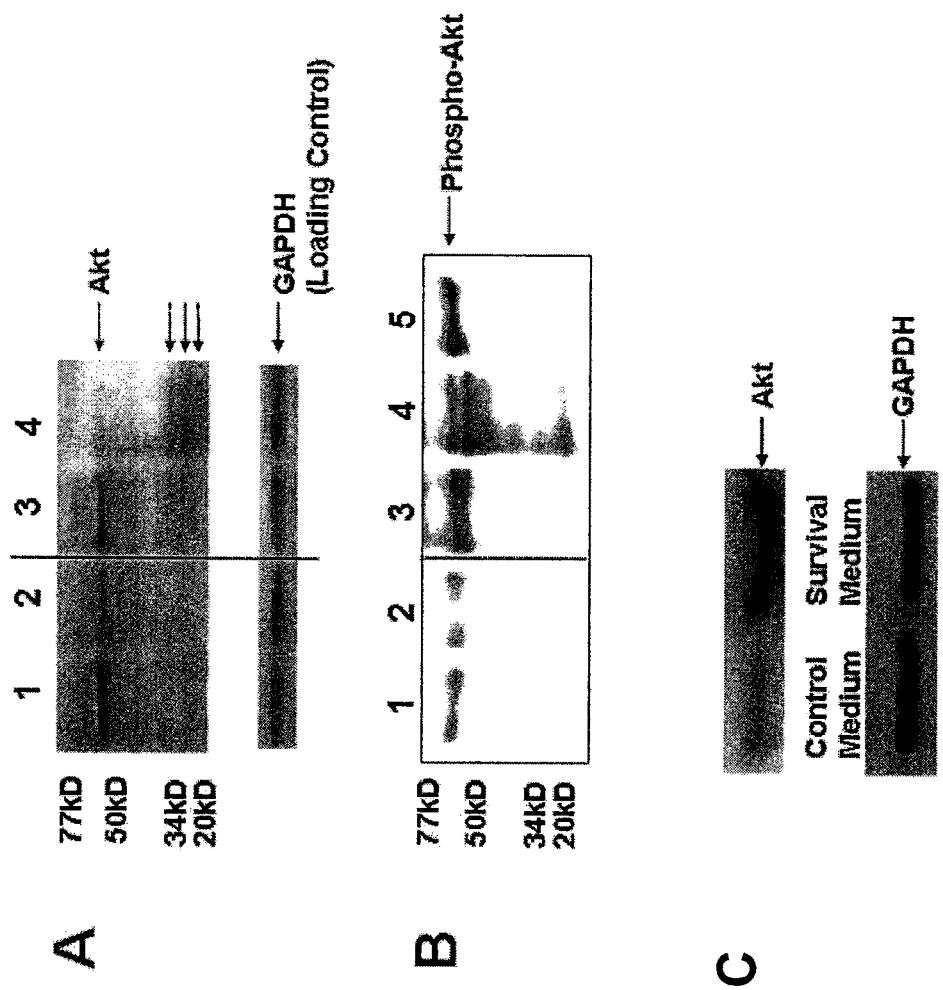
FIG. 4(A-C). Figures A and B show immunoblot analysis carried out on whole cell lysates prepared fro cultured pancreatic cells (3 days after seeding) and probed with anti-Akt antibodies (FIG. 4A) or anti-Akt Ser473 phospho-specific antibodies (FIG. 4B). Immunoblots of untreated fibroblasts (figures A and B lane 1) fibroblasts treated with staurosporine (figures A and B lane 2) and the adherent (Figure A and B lane 3) and the non-adherent (figures A and B lane 4) fractions of pancreatic cell cultures are shown. Control lysate of pancreatic culture treated with 100 nM PDGF was included as a control (figure B lane 5).

Immunoblot analysis with the anti-phosphoserine-473 antibody revealed that full length Akt was phosphorylated and presumably active in adherent pancreatic cells (FIG. 4B). Phosphorylated fragments were also notable in the non-adherent cells, and to a lesser degree in the adherent population. Addition of PDGF-BB (R &D Systems, Minneapolis, Minn.) (50 ng/ml) to the cultures resulted in an intensification of the full-length, phosphorylated Akt (see FIG. 4). These results indicate that dephosphorylation of Akt is not a requirement for caspase inactivation of Akt; and furthermore, that phosphorylated and activated Akt fragments can play a role during apoptosis.

Example 5

Phenotypic Assays of Cells Treated and Expanded in Survival Media

A. Immunofluorescence.

Figure 3:
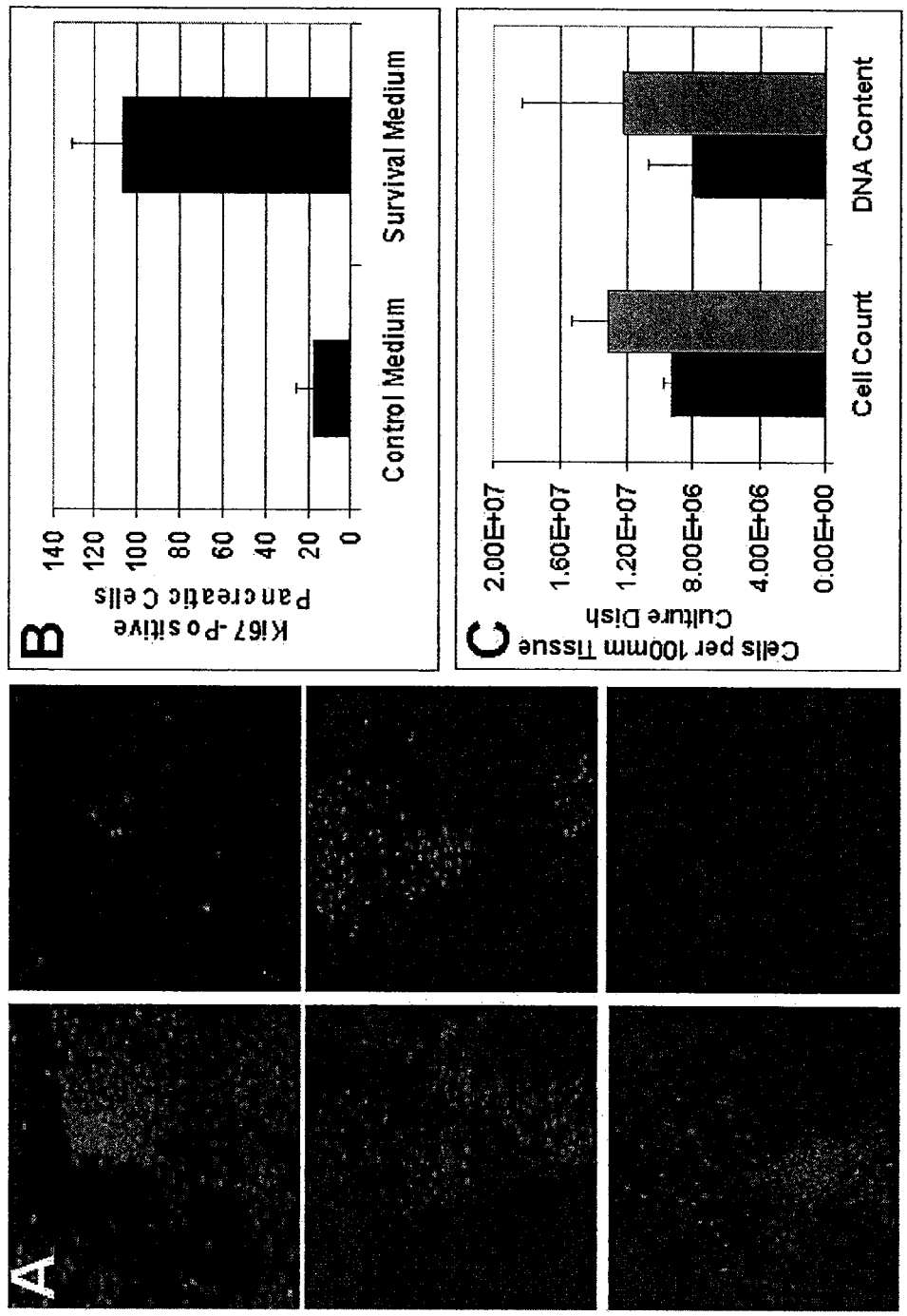
FIG. 3(A-C) illustrates proliferation of pancreatic cells cultured in survival medium.

To determine the effects of survival media on proliferation of pancreatic cells, we examined expression of Ki-67 protein, a marker of proliferating cells (FIG. 3). For immunofluorescence, cells were grown in 4-well chamber slides and log phase cells were fixed in 4% paraformaldehyde at room temperature. Cells were incubated in blocking buffer (PBS/3% BSA/1% normal goat serum) for 1 hr, subsequently permeabilized with PBS/0.2% TritonX for 5 minutes and then washed and incubated with a polyclonal guinea pig anti-human C-peptide antibody (DAKO) for 1 hr, or antibodies against Ki67 diluted 1:500 (Neomarkers, Fremont, Calif.). The cells were washed three times for 15 minutes each with PBS/1% TritonX/1% BSA and incubated in secondary Alexafluor 488-conjugated antibody (1:200) (Molecular Probes, Carlsbad, Calif.) for 1 hr. Cells were then washed for 15 minutes and fixed again in 4% paraformaldehyde. After washing in PBS/RNAse for 5 minutes, the cells were mounted using Vectashield containing DAPI nuclear stain (Vector Labs, Burlingame, Calif.). The results show a dramatic increase in the number of Ki67 positive cells; and, hence, a much greater proliferation rate of cells expanded in survival media. The use of survival media thus represents a method of maximizing the starting cell population from scarce organ donors by rapid expansion of the endocrine lineage population.

B. Immunohistochemistry.

Figure 5:
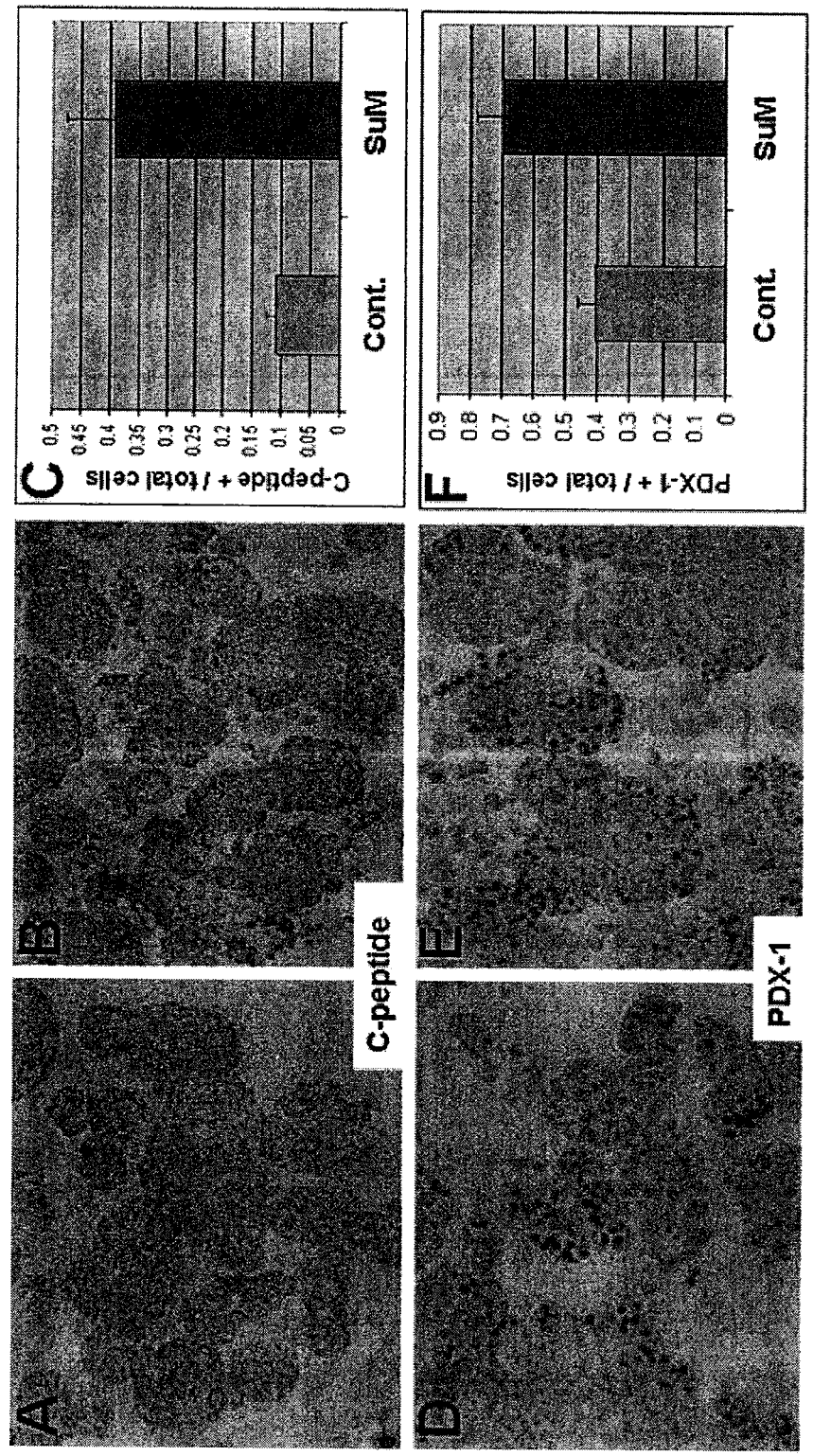
FIG. 5(A-F) shows increased C-peptide and PDX-1 immunolabeling in pancreatic cells after treatment with survival medium. Figures A-D show immunocytochemistry carried out on paraffin embedded sections of pancreatic cell aggregates from cells growth either in control medium (panels A and D) or survival medium (panels B and E). Anti-C-peptide staining is shown in the upper panels and anti-PDX-1 staining is shown in the lower panels. The percentage of C-peptide (+) cells (panel C) and PDX-1 (+) cells (panel F) are shown. The experiments were done in triplicate and the quantification represents an average of four independent fields.

To further examine the effects of survival media on the endocrine lineage population, we examined expression of insulin and PDX protein levels in these cells (FIG. 5). Pancreatic cells were washed in Dulbecco's phosphate buffered saline (DPBS), fixed in Bouin's fluid for 1 hr., dehydrated in a graded series of alcohols, and processed for paraffin embedding. Four μm-thick paraffin sections were cut and placed on glass slides. Slides were processed using standard histological techniques followed by incubation in 0.3% $H_2O_2$ to quench endogenous peroxidase activity. All slides were blocked in 10% species-appropriate, normal serum. Primary antibodies were reacted with tissue sections for 60 minutes at room temperature using the following dilutions: guinea pig anti-C-peptide (1:2000; DAKO, Carpinteria, Calif.), rabbit anti-PDX-1 (1:1000; Incstar, Stillwater, Minn.). (FIG. 5). Antibody binding specificity was controlled by substituting primary antibody with the corresponding dilution of the respective normal sera or non-specific IgG. Slides were then incubated with the appropriate biotinylated secondary antibody (Vector Lab, Burlingame, Calif.) according to manufacturer's instructions. Antibody binding was visualized by using an ABC/DAB kit (DAKO), and tissue sections were counterstained in hematoxylin. The results indicate that in the cell populations expanded with survival media, more cells stained positive for C-peptide and PDX-1. These results corroborate our earlier finding that more endocrine cells are present in cells treated with survival media as demonstrated by RT-PCR and immunofluorescence staining.

C. Real-Time Quantitative RT-PCR

Figure 6:
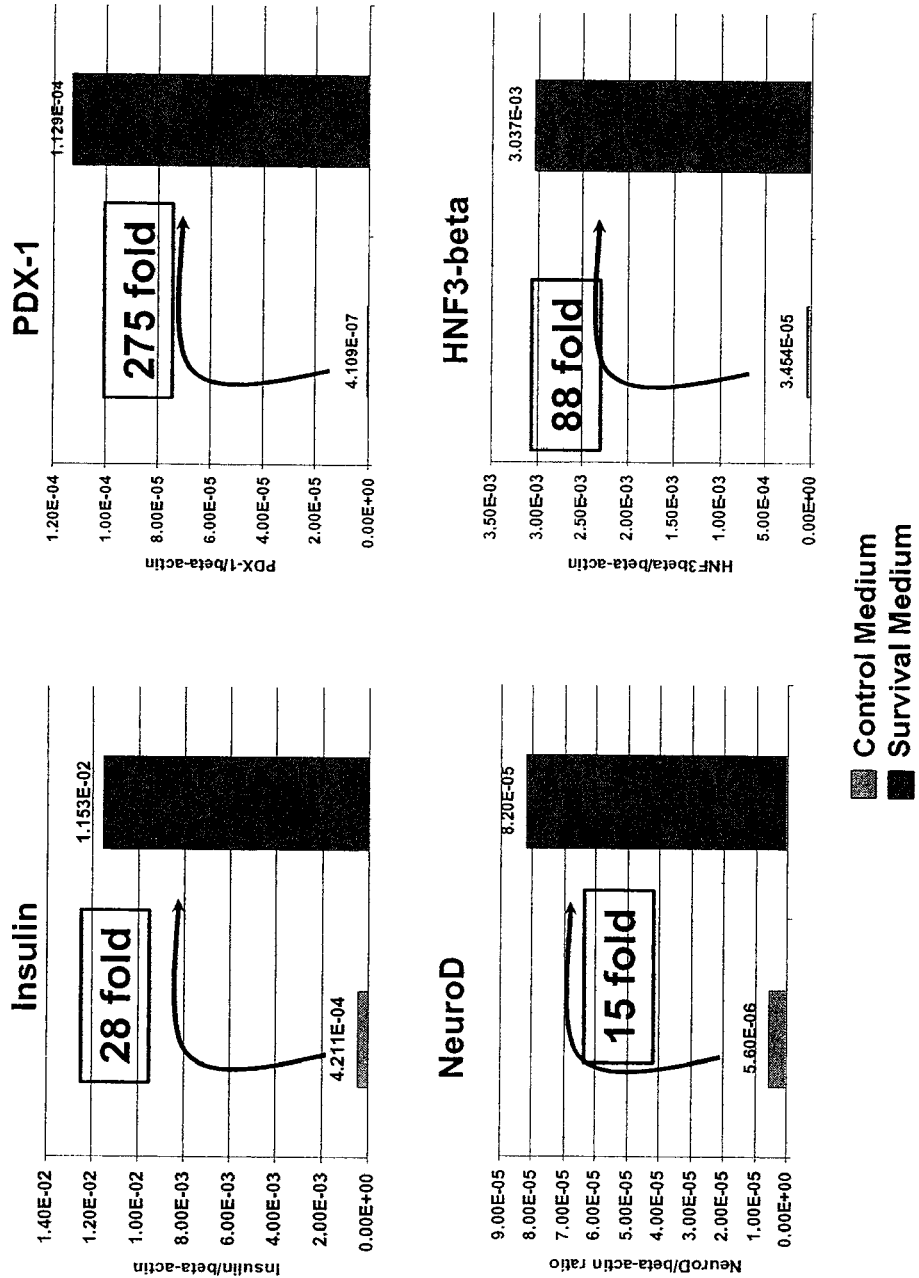
FIG. 6(A-D) illustrates that pancreatic cells grown in survival medium show increased expression of endocrine and progenitor markers. RNA lysates of human pancreatic cells passaged three times and maintained in either control medium (left bar in each panel) or survival medium (right bar in each panel) were analyzed by qRT-PCR for expression of insulin, NeuroD, PDX-1 and HNF3-β. Gene expression is shown as a ratio of the gene to β-actin mRNA. Data is also expressed as the fold increase in the ratio in survival media as compared to control. For example, insulin showed a 28-fold increase in cells grown in survival medium as compared to cells grown in control medium. Similarly, NeuroD showed a 15-fold increase, PDX-1 a 275-fold increase and HNF3-β an 88-fold increase as compared to cells grown in control media.

To determine the effects of survival media on endocrine lineage cells, we studied the gene expression of our expanded pancreatic cells by quantitative RT-PCR as shown for example in FIG. 6. Total cellular RNA was isolated from cells using Nucleospin RNA II kits (BD Biosciences, Inc.). Reverse transcription was performed using 5 μg of total RNA M-MLV reverse transcriptase (Invitrogen), 10 mM DTT, 0.5 mM dNTP (Sigma, St. Louis, Mo.), 25 ng/μl of Oligo(dt) 12-18 primer (Sigma), RNase inhibitor (Sigma) and 1× First-strand buffer (Invitrogen). The mixture was heated to 65° C. for 5 minutes. Reverse transcriptase was added and incubated at 37° C. for 60 minutes. Reactions were terminated and real-time quantitative PCR was performed according to the manufacturer's instructions using Light Cycler machines 1.0 and 2.0 (Roche) in the presence of 0.5 ml of 5-fold diluted cDNA. Insulin, glucagon, Somatostatin, PDX-1, Neuro-D1, CK-19, amylase, HNF3-beta, and β-actin primer sequences were designed based on published human mRNA sequences. Data for mRNA was presented according to calculations using absolute quantification methods, or as a fold increase over the control. All expression levels of the different genes were normalized to β-actin. The increase in endocrine and progenitor marker gene expression in cells expanded in survival media indicates that an endocrine lineage population was being preserved and expanded (see, e.g., FIG. 6). Thus, the pancreatic endocrine cells have increased proliferation and survival rates in the survival media as compared to the proliferation and survival rates in the control media.

Example 6

Functional Assays of Cells Treated and Expanded in Survival Media

A. Cell Microencapsulation.

Upon cell expansion it is necessary to differentiate cells to assess the function of terminally differentiated beta cells. Alginate cell encapsulation serves as a model of differentiation wherein encapsulated single cells aggregate and become terminally differentiated in the presence of DM. The harvested cells were suspended in a 1.6% (w/v) sodium alginate solution and encapsulated in alginate-poly-L-lysine (PLL)-alginate microcapsules using an air-jet as described (Soon-Shiong et al., *Transplantation* 54:769-74, (1992)). To promote cell aggregation, the gelled alginate core within the nascent capsules was liquefied by incubating capsules in 55 mM sodium citrate (pH 7.2, 290 mOsm/kg). The resulting encapsulated cell aggregates were placed in tissue culture flasks containing SM95 medium. After the cells recovered, media was changed to DM (differentiation media). Thereafter, complete medium changes were performed twice per week. After 1-3 weeks in culture, encapsulated cell aggregates were used for static glucose stimulation (see, e.g., FIG. 8).

B. Static Glucose Stimulation (SGS) Assay

To examine the effects of survival media on the function of beta cells, encapsulated cells (200-250 microcapsules) were incubated overnight (at 37° C., 5% CO2) with 5 ml of low glucose (100 mg/dl), insulin-deficient culture medium. The encapsulated cells were tested for functionality by successive 60 minute incubations (at 37° C., 5% CO2) in Krebs Ringer solutions supplemented with: 60 mg/dl glucose (low 1), 450 mg/dl glucose (Sigma) (High), and 60 mg/dl glucose (low 2). After each step, solutions were collected and stored for subsequent analysis. After the final step, capsules were counted under a dissecting scope. Human C-peptide content of each solution was quantified using an ultra sensitive C-peptide ELISA (Mercodia, Uppsala, Sweden) according to the manufacturer's instructions. C-peptide release is expressed as accumulation per ml of buffer (collected following each incubation step) or as a relative stimulation index (SI) which is the secretion of insulin obtained in high glucose solution (High) divided by that obtained in low glucose (Low I). Values were normalized to capsules number which contained equal numbers of cells per capsule. The results shown in FIGS. 8A and B indicate a higher response to glucose challenge in cells that were expanded in survival media, as well as higher endocrine gene expression, supporting the finding that we have enriched for endocrine lineage cells and that expansion in survival media did not compromise their function.

What is claimed is:

1. A method of improving insulin or glucagon production in mature pancreatic endocrine cells in a pancreatic cell culture comprising
contacting pancreatic endocrine cells with (1) an exogenous caspase inhibitor in an amount sufficient to reduce apoptosis in the pancreatic endocrine cells; and (2) at least one exogenous growth factor in an amount sufficient to increase the level of activated Akt in the pancreatic endocrine cells; and
differentiating the pancreatic endocrine cells contacted with (1) and (2) into mature pancreatic endocrine cells that express insulin and/or glucagon at a synergistically higher level than differentiated pancreatic endocrine cells contacted only with (1) or (2), wherein glucagon and/or insulin are as measured by qPCR analysis of insulin mRNA or glucagon mRNA, respectively, and wherein the qPCR results are as displayed as the ratio of insulin mRNA to β-actin mRNA, or glucagon mRNA to actin mRNA, respectively.

2. The method of claim 1, wherein the pancreatic endocrine cells are insulin producing aggregates.

3. The method of claim 1 wherein the caspase inhibitor is selected from the group consisting of: Q-VD-OPH, Z-VAD (OMe)-FMK, Ac-VAD-CHO, Boc-D-FMK, BACMK, BI-9B12, Ac-LDESD-CHO, and DEVD-CHO CPP32/Apopain Inhibitor.

4. The method of claim 1, wherein the concentration of caspase inhibitor is from about 1 μm to about 100 μm.

5. The method of claim 1, wherein the caspase inhibitor is an irreversible pan caspase inhibitor, selected from the group consisting of Q-VD-OPH and Z-VAD (OMe)-FMK.

6. The method of claim 5, wherein the caspase inhibitor is Q-VD-OPH.

7. The method of claim 1, wherein the growth factor is selected from the group consisting of EGF, IGF-I, IGF-II, heregulin, and PDGF-BB.

8. The method of claim 1, wherein the growth factor is PDGF-BB and one or more members of the group consisting of IGF-I and IGF-II.

9. The method of claim 8, wherein the concentration of each growth factor is from about 10 ng/ml to about 100 ng/ml of culture medium.

10. The method of claim 1, wherein the pancreatic endocrine cells are progenitor pancreatic endocrine cells.

* * * * *

SEQUENCE LISTING

<160> NUMBER OF SEQ ID NOS: 1

<210> SEQ ID NO 1
<211> LENGTH: 4
<212> TYPE: PRT
<213> ORGANISM: Homo Sapiens

```
<400> SEQUENCE: 1

Asp Glu Val Asp
1
```